(12) United States Patent
Lee

(10) Patent No.: US 6,537,988 B2
(45) Date of Patent: Mar. 25, 2003

(54) SYNERGISTIC METHODS AND COMPOSITIONS FOR TREATING CANCER

(75) Inventor: Francis Y. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/817,456

(22) Filed: Mar. 26, 2001

(65) Prior Publication Data
US 2002/0002162 A1 Jan. 3, 2002

Related U.S. Application Data
(60) Provisional application No. 60/192,278, filed on Mar. 27, 2000.

(51) Int. Cl.[7] ............................................. A61K 31/55
(52) U.S. Cl. ................................. 514/221; 514/2; 514/8; 514/449; 514/922
(58) Field of Search .......................... 514/221, 449, 514/922, 2, 8

(56) References Cited

U.S. PATENT DOCUMENTS

6,011,029 A * 1/2000 Ding et al. ................. 514/221
6,136,462 A1 * 11/2001 Bishop et al. .............. 514/290

FOREIGN PATENT DOCUMENTS

| WO | WO 98/54966 | 12/1998 |
|---|---|---|
| WO | WO 99/32114 | 7/1999 |
| WO | WO 00/42849 | 7/2000 |

OTHER PUBLICATIONS

Moasser et al., "Farnesyl transferase inhibitors cause enhanced mitotic sensitivity to taxol and epothilones," Proc. Natl. Acad. Sci. USA, vol. 95, pp. 1369–1374, Feb. 1998.

Hunt, John T., et al. , J. Med. Chem (2000), 43(20), 3587–3595, XP002191598.

* cited by examiner

Primary Examiner—Frederick Krass
(74) Attorney, Agent, or Firm—Maureen S. Gibbons

(57) ABSTRACT

The present invention provides a synergistic method for the treatment of cancer which comprises administering to a mammalian specie in need thereof a synergistically, therapeutically effective amount of: (1) at least agent selected from the group consisting of cytotoxic agents and cytostatic agents, and (2) a compound of formula I

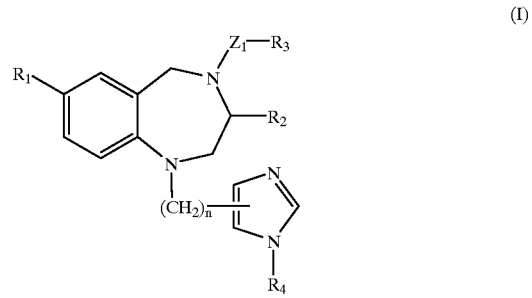

or a pharmaceutically acceptable salt thereof. The present invention further provides a pharmaceutical composition for the synergistic treatment of cancer which comprises at least one agent selected from the group consisting of antiproliferative cytotoxic agents and antiproliferative cytostatic agents, a compound of formula I, and a pharmaceutically acceptable carrier.

53 Claims, 21 Drawing Sheets

Combination chemotherapy with Compound 1 + Compound 2

Combination chemotherapy with Compound 1 + Compound 2

Combination chemotherapy with Compound 1 + Compound 2

Combination chemotherapy with paclitaxel + Compound 2

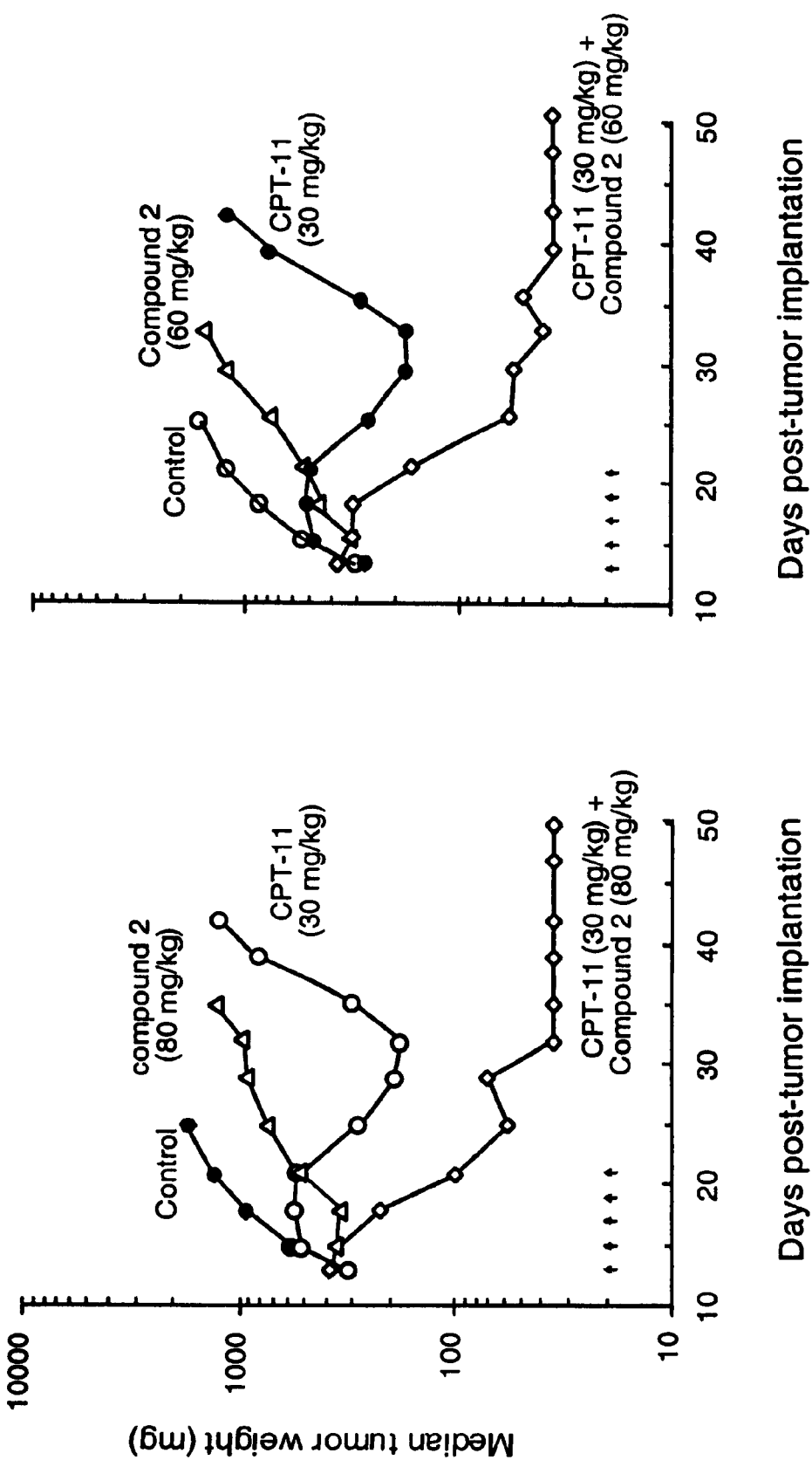

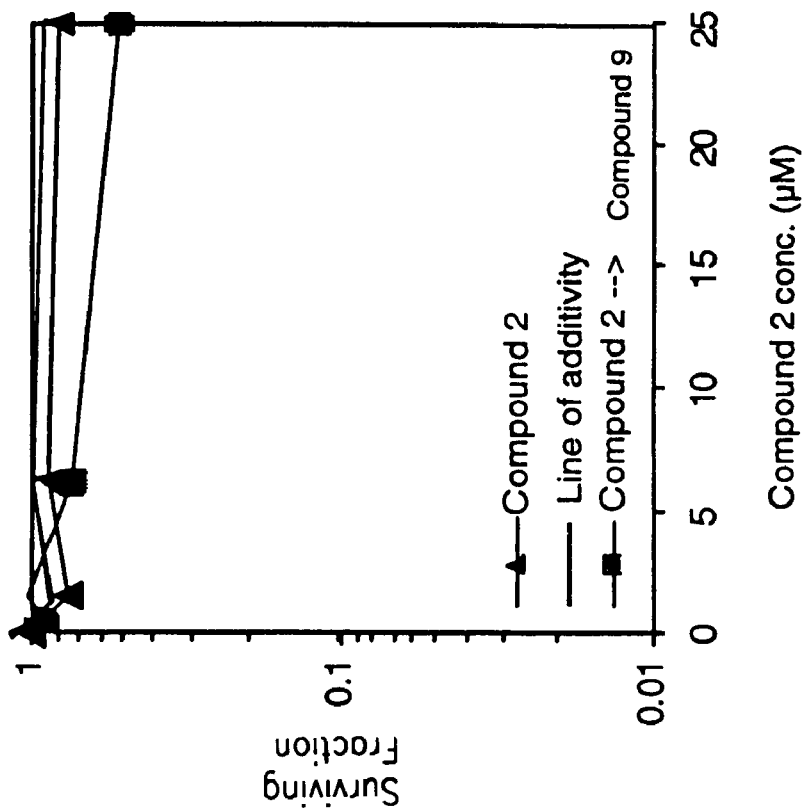
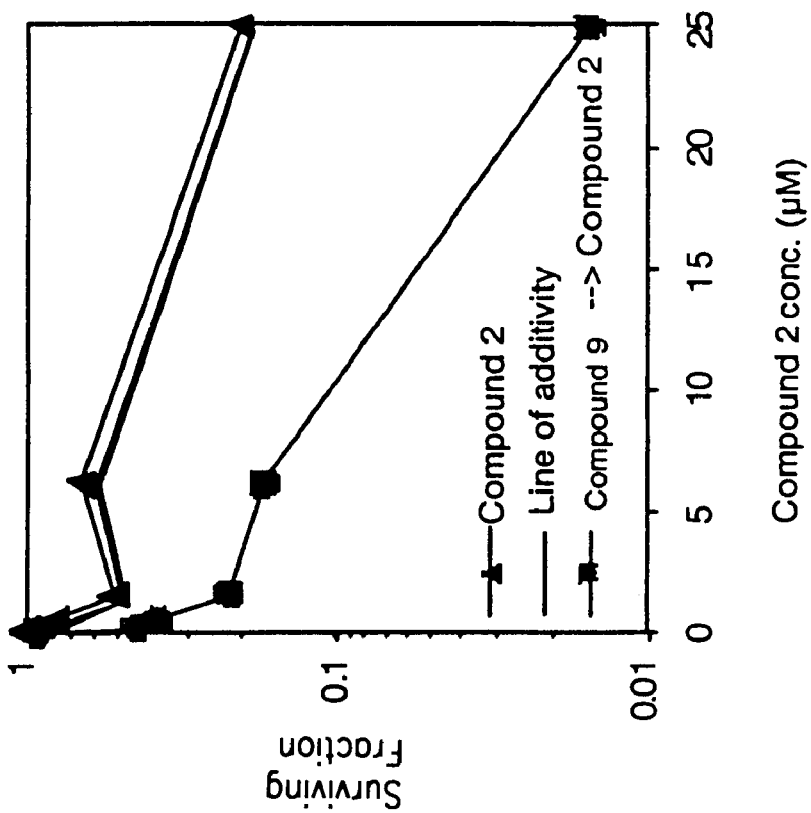
FIG. 23A
FIG. 23B

SYNERGISTIC METHODS AND COMPOSITIONS FOR TREATING CANCER

RELATED APPLICATIONS

This application claims priority benefit under Title 35 § 119(e) of U.S. Provisional Application No. 60/192,278, filed Mar. 27, 2000, and entitled SYNERGISTIC METHODS AND COMPOSITIONS FOR TREATING CANCER.

FIELD OF THE INVENTION

The present invention relates to therapies for treatment of cancer, specifically to the synergistic use of two or more anti-cancer agents having antiproliferative cytotoxic and cytostatic activities.

BACKGROUND OF THE INVENTION

Chemotherapy, the systemic administration of antineoplastic agents that travel throughout the body via the blood circulatory system, along with and often in conjunction with surgery and/or radiation treatment, has for years been widely utilized in the treatment of a wide variety of cancers. Unfortunately, the available chemotherapeutic drugs often fail patients because they kill many healthy cells and thus bring on serious side effects that limit the doses physicians can administer.

In particular, cancerous tumors are difficult to treat because they contain both proliferating and non-proliferating cancer cells. As a cancerous tumor grows, the vascular development often cannot keep pace with the rapid proliferation of malignant cell population. Consequently, solid cancerous tumor masses typically exhibit abnormal blood vessel networks which, unlike vessels in normal tissues, fail to provide adequate nutritional support to the cancerous tumor cells for optimal growth. In most cancerous, solid tumors, non-proliferating tumor cells constitute the majority of the total tumor cell population. Moreover, as a tumor grows in size the proportion of non-proliferating tumor cells also increases in proportion. As most current anti-cancer agents target proliferating cells, the non-proliferating tumor cell population has been implicated as a major contributing factor in the failure of radiation or chemotherapy used alone or together to cure neoplastic disease.

As mentioned above, as a tumor grows in size, it typically becomes more refractory to most chemotherapies. Accordingly, many tumor eradication procedures include a debulking step to decrease the mass of the tumor prior to the administration of anti-neoplastic agents. However, debulking does not always result in tumor eradication, even when combined with powerful chemotherapeutic agents. Accordingly, there is a need in the art for new treatments that target both proliferating and non-proliferating cancer cells for the treatment of malignancy.

WO 98/54966 discloses combination therapies employing an antineoplastic agent or radiation therapy in conjunction with an inhibitor of prenyl-protein transferase which may be useful in the treatment of cancer. However, WO 98/54966 does not disclose the use of the formula I compounds of the present invention.

U.S. Pat. No. 6,011,029 discloses the formula I compounds of the present invention and provides methods for their use as anti-cancer agents. In addition, that patent generically discloses that the formula I compounds may be useful in combination with other cancer therapies. However, U.S. Pat. No. 6,011,029 does not disclose any specific combination treatments nor does it disclose or suggest combination treatments which act synergistically as anti-cancer treatments.

It is, therefore, an object of the present invention to provide a synergistic method for the treatment of cancer.

It is also an object of the present invention to provide a pharmaceutical composition for the synergistic treatment of cancer.

Those and other objects of the present invention will become more apparent from the description thereof set forth below.

SUMMARY OF THE INVENTION

The present invention provides a synergistic method for the treatment of cancer which comprises administering to a mammalian specie in need thereof a synergistically, therapeutically effective amount of: (1) at least one agent selected from the group consisting of anti-proliferative cytotoxic agents and anti-proliferative cytostatic agents, and (2) a compound of formula I

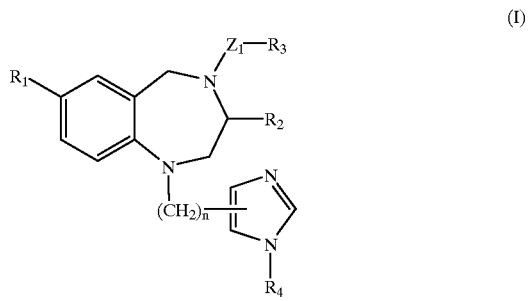

or a pharmaceutically acceptable salt thereof wherein
$R_1$ is Cl, Br, CN, optionally substituted phenyl, or optionally substituted 2-,3- or 4-pyridyl;
$R_2$ is optionally substituted lower alkyl, or optionally substituted aralkyl;
$R_3$ and $R_5$ are each independently optionally substituted lower alkyl, optionally substituted aryl, or optionally substituted heterocyclo;
$R_4$ is hydrogen or lower alkyl;
$Z_1$ is CO, $SO_2$, $CO_2$ or $SO_2N(R_5)$—; and
n is 1 or 2;
provided that the cytotoxic agent and/or cytostatic agent is administered simultaneous with or prior to the formula I compound.

The present invention further provides a pharmaceutical composition for the synergistic treatment of cancer which comprises at least one agent selected from the group consisting of anti-proliferative cytotoxic agents and anti-proliferative cytostatic agents, and a compound of formula I, and a pharmaceutically acceptable carrier.

In a preferred embodiment of the invention the cytotoxic or cytostatic agent is administered prior to the administration of a compound of formula I. In another embodiment of the invention, the cytotoxic or cytostatic agent is administered simultaneously with the compound of formula I.

BRIEF DESCRIPTION OF THE FIGURES

FIGS. 15(A) and 15(B) demonstrate that combination chemotherapy with Compound 2 and CPT-11 produced synergistic antitumor activity in an advanced (300–500 mg) human colon carcinoma HCT116 grown in nude mice. CPT-11 was administered 1 hour before Compound 2. CPT-11 was administered IV at or near its MTD of 30 mg/kg/inj. Compound 2 was given at two different dose levels: 60 and 80 mg/kg/inj, IV.

FIG. 18A: Clonogenic survival of the SAL-2 cell line following exposure to paclitaxel for 20 hours at the indicated concentrations.

FIG. 18B, Clonogenic survival of the SAL-2 cell line following exposure to Compound 2 for 20 hours at the indicated concentrations.

FIG. 18C: Antagonistic interaction between paclitaxel and the Her-1 inhibitor, Compound 8. SAL-2 cells were first exposed to Compound 8 for 20 hour before further exposure to paclitaxel for an additional 20 hours.

FIG. 18D: Synergistic interaction between Compound 2 and the Her-1 inhibitor, Compound 8. SAL-2 cells were first exposed to Compound 9 for 20 hour before further exposure to Compound 2 for an additional 20 hours. Compound 2 enhances the antitumor activity of the Her-1 (EGFR) inhibitor Iressa® in the Her-1 overexpressing A431 human squamous cell carcinoma xenograft model in nude mice.

FIG. 18E: Combined effects of Iressa® (200 mg/kg/adm, PO, Q1D×11) and Compound 2 (60 mg/kg/inj., IV, Q2D×5). Iressa® therapy was initiated 3 days prior to the beginning of treatment with Compound 2.

FIG. 18F: Combined effects of Iressa® (200 mg/kg/adm, PO, Q1D×11) and Compound 2 (80 mg/kg/inj., IV, Q2D×5).

FIG. 18G: Combined effects of Iressa® (200 mg/kg/adm, PO, Q1D×11) and Paclitaxel (24 mg/kg/inj., IV, Q2D×5).

FIG. 23 demonstrates that the combination of the CDK inhibitor (CDKI), Compound 9, with Compound 2 produced sequence-dependent, synergistic cytotoxic effects on A2780 human ovarian cancer cells in vitro.

FIG. 23(A), 4 hour treatment with 1.5 $\mu$M Compound 9 (no effect dose) was combined with a 20 hour treatment of increasing concentrations of Compound 2. Colony formation was scored on day 10. Panel A. CDKI treatment preceded Compound 2.

FIG. 23(B), Panel B, Compound 2 treatment preceded CDKI.

DETAILED DESCRIPTION OF THE INVENTION

Figure 1:
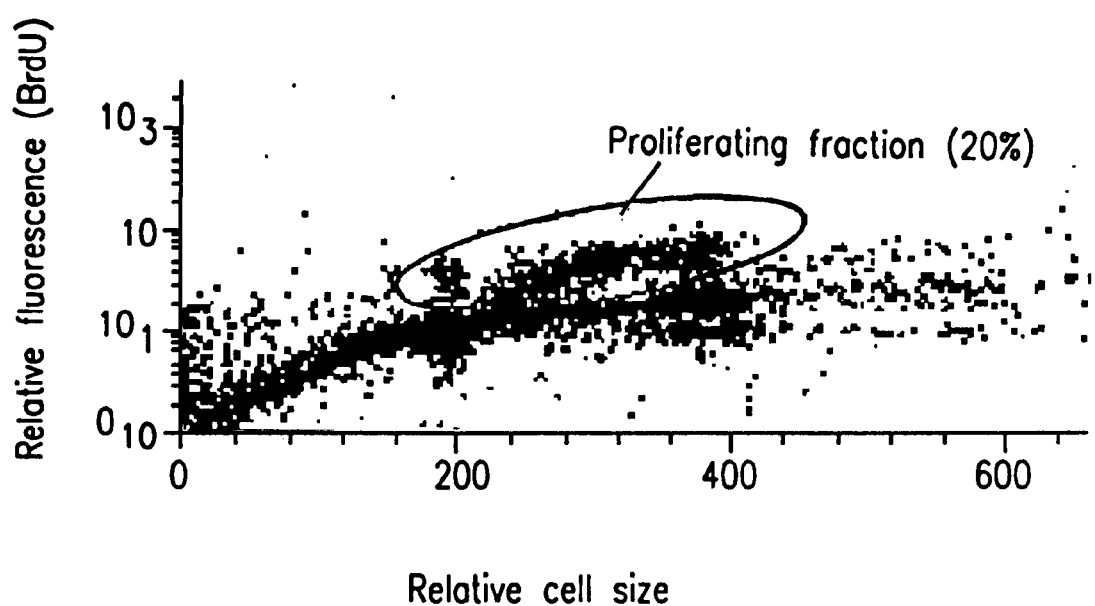
FIG. 1 illustrates that, in the HCT116 solid human colorectal carcinoma model grown in nude mice, the vast majority of the tumor cells are in the non-proliferative ($G_0$) growth stage. Non-proliferative cells present in a HCT-116 human colon carcinoma solid tumor grown subcutaneously were identified by prolonged BrdUrd labeling (24 h) by continuous infusion. Only 20% of the total population of the tumor cells dispersed from the solid tumor stained positive for BrdUrd, which selectively labels proliferating cells.

Advantageously, the present invention provides a method for the synergistic treatment of cancer which comprises administering a synergistically, therapeutically effective amount of: (1) at least one agent selected from the group consisting of an anti-proliferative cytotoxic agent, and an anti-proliferative cytostatic agent, and (2) a compound of formula I to a mammalian specie, preferably a human, in need thereof.

Surprisingly, it has been found that the use of: (1) at least one anti-proliferative cytotoxic agent and/or anti-proliferative cytostatic agent, and (2) a compound of formula I when used in combination provides a synergistic method for the treatment of cancer. As used herein, the term "synergistic" means that the effect achieved with the methods and compositions of this invention is greater than the sum of the effects that result from methods and compositions comprising the cytotoxic or cytostatic agent or agents, and formula I compound of this invention separately and in the amounts employed in the methods and compositions hereof. Advantageously, such synergy between the active ingredients allows for the use of smaller doses of one or both active ingredients, allows for the use of lower doses of the antineoplastic agents or agent or radiation therapy, provides greater efficacy at the same doses, and/or prevents or delays the build-up of multi-drug resistance.

Further advantages over previously disclosed methods include the ability of the instant combination of compounds of formula I and at least one agent selected from the group consisting of a cytostatic agent and a cytotoxic agent(s) to be individually varied depending on the nature of the cancer cells to be treated. It is also anticipated that the therapeutic effect of the instant compositions may be achieved with smaller amounts of the cytotoxic or cytostatic agent(s) and compounds of formula I than would be required if such antineoplastic agents and compounds of formula I were administered alone. This approach avoids any non-mechanism-based adverse toxicity effects which might result from administration of an amount of an antineoplastic agent or agents or a compound of formula I or radiation therapy alone sufficient to achieve the same therapeutic effect. The instant compositions achieve a synergistic therapeutic effect and exhibit unexpected therapeutic advantage over the effect of any of the component compounds or methods when administered alone.

The extent of selectivity of the two or more anti-cancer agents that comprise the method of the instant invention provide therapeutic advantages over previously disclosed methods of using a single antineoplastic agent for the treatment of cancer. In particular, use of two or more independent pharmaceutically active components that have complementary, essentially non-overlapping activities allows the person utilizing the instant method of treatment to independently and accurately vary the activity of the combination without having to synthesize a single drug having a particular pharmaceutical activity profile. In addition, such combinations should effectively target both proliferative and non-proliferative cells.

The anti-proliferative cytotoxic agent(s) which includes radiation therapy, may be administered simultaneously with or prior to the formula I compound. In a preferred embodiment of the present invention, the anti-proliferative cytotoxic agent(s) and/or radiation therapy is administered prior to the formula I compound. As used herein, the term "simultaneous" or "simultaneously" means that the antiproliferative cytotoxic agent(s) or radiation therapy and the formula I compound are administered within 24 hours, preferably 12 hours, more preferably 6 hours, and most preferably 3 hours or less, of each other.

In addition to the anti-proliferative cytotoxic agent(s) and radiation therapy described above, agents which cause cells to become "non-proliferative" or "quiescent," referred to herein as "anti-proliferative cytostatic agents" or "quiescence agents," may optionally be administered to a patient in need thereof. The anti-proliferative cytostatic agents may be administered simultaneously or sequentially with the compound of formula I or the radiation therapy or cytotoxic agent(s).

The present invention provides methods for the synergistic treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

Most preferably, the invention is used to treat accelerated or metastatic cancers of the bladder, pancreatic cancer, prostate cancer, non-small cell lung cancer, colorectal cancer, and breast cancer.

In a preferred embodiment of this invention, a method is provided for the synergistic treatment of cancerous tumors. Advantageously, the synergistic method of this invention reduces the development of tumors, reduces tumor burden, or produces tumor regression in a mammalian host.

As used herein, the phrase "radiation therapy" includes, but is not limited to, x-rays or gamma rays which are delivered from either an externally applied source such as a beam or by implantation of small radioactive sources. Radiation therapy may also be considered an anti-proliferative cytotoxic agent.

As used herein, the phrase "anti-neoplastic agent" is synonymous with "chemotherapeutic agent" and refers to compounds that prevent cancer cells from multiplying (i.e. anti-proliferative agents). In general, the agent(s) of this invention fall into two classes, anti-proliferative cytotoxic and anti-proliferative cytostatic. Cytotoxic agents prevent cancer cells from multiplying by: (1) interfering with the cell's ability to replicate DNA and (2) inducing cell death and/or apoptosis in the cancer cells. Anti-proliferative cytostatic or quiescent agents act via modulating, interfering or inhibiting the processes of cellular signal transduction which regulate cell proliferation. The majority of chemotherapeutic agents are cytotoxic and target proliferating cells.

Classes of compounds that may be used as anti-proliferative cytotoxic agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxycoformycin, Mitomycin-C, L-Asparaginase, Interferons (especially IFN-a), Etoposide, and Teniposide.

Other anti-proliferative cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their anti-proliferative cytotoxic activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in the scientific and patent literature, see, e.g., Bulinski (1997) *J. Cell Sci.* 110:3055 3064; Panda (1997) *Proc. Natl. Acad. Sci. USA* 94:10560–10564; Muhlradt (1997) Cancer Res. 57:3344–3346; Nicolaou (1997) *Nature* 387:268–272; Vasquez (1997) *Mol. Biol. Cell.* 8:973–985; Panda (1996) *J. Biol. Chem* 271:29807–29812.

The term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) *Oncology*, 6: 17–23, Horwitz (1992) *Trends Pharmacol. Sci.* 13: 134–146, Rowinsky (1990) *J. Natl. Canc. Inst.* 82:1247–1259).

Particularly preferred anti-proliferative cytotoxic agents are compounds with paclitaxel-like activity. These include, but are not limited to, paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

Thus, anti-proliferative cytotoxic agents which are suitable for use in the methods and compositions of this invention include, but are not limited to, microtubule-stabilizing agents such as paclitaxel (also known as Taxol®), docetaxel (also known as Taxotere®), 7-O-methylthiomethylpaclitaxel (disclosed in U.S. Pat. No. 5,646,176), 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 60/179,965 filed on Feb. 3, 2000, and example 17 herein), C-4 methyl carbonate paclitaxel (disclosed in WO 94/14787), epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0] heptadecane-5,9-dione (disclosed in WO 99/02514), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione (disclosed in U.S. Ser. No. 09/506,481 filed on Feb. 17, 2000, now U.S. Pat. No. 6,262,094, and examples 7 and 8 herein), and derivatives thereof; and microtubule-disruptor agents.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Additional anti-proliferative cytotoxic agents include, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin® (trastuzumab). Some especially preferred anti-proliferative cytostatic agents are paclitaxel, cis-platin, carboplatin, epothilones, gemcytabine, CPT-11,5-fluorouracil, tegafur, leucovorin, and EGFR inhibitors such as Iressa® (ZD 1839, 4-(3-chloro-4-fluorophenylamino)-7-methoxy-6-(3-(4-morpholinyl)propoxy)quinazoline and OSI-774 (4-(3-ethynylphenylamino)-6,7-bis(2-methoxyethoxy)quinazoline).

In one embodiment of this invention, proliferative cancer cells are rendered non-proliferative before or during treatment with the present invention by treatment with a cytostatic agent. As used herein, "cytostatic agent" is synonymous with "quiescence agent" and refers to any means of slowing the rate of cell division or tumor growth so that the cells become non-proliferative or so that their behavior approximates that of non-proliferative cells. Exemplary antiproliferative cytostatic or "quiescent" agents of the invention, include without limitation, hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, hlorotrianisene, Hydroxyprogesterone, Aminoglutethimide, Estramustine, Medroxyprogesteroneacetate, Leuprolide, Flutamide, Toremifene, Zoladex.

Also suitable for use as cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an antiproliferative cytostatic agent is Casodex® (bicalutamide, Astra Zeneca) which renders androgen-dependent carcinomas non-proliferative. Yet another example of a cytostatic agent is the antiestrogen Tamoxifen which inhibits the proliferation or growth of estrogen dependent breast cancer. Inhibitors of the transduction of cellular proliferative signals are cytostatic agents. Examples are epidermal growth factor inhibitors, Her-2 inhibitors, MEK-1 kinase inhibitors, MAPK kinase inhibitors, PI3 inhibitors, Src kinase inhibitors, and PDGF inhibitors.

As mentioned, cytostatic agents also comprise antiangiogenic and antivascular agents which, by interrupting blood flow to solid tumors, render cancer cells quiescent by depriving them of nutrition. Castration, which also renders androgen dependent carcinomas non-proliferative, may also be utilized. Starvation by means other than surgical disruption of blood flow is another example of a cytostatic agent. A particularly preferred class of antivascular cytostatic agents is the combretastatins. Other exemplary cytostatic agents include MET kinase inhibitors, MAP kinase inhibitors, inhibitors of non-receptor and receptor tyrosine kinases, inhibitors of integrin signaling, and inhibitors of insulin-like growth factor receptors.

In preferred embodiments of the invention, the method entails administration of a combination of two or more antineoplastic agents. For example, the date presented herein show that the human prostate cancer MDA-PCa-2b xenografts are rendered quiescent by surgically castrating the host animals prior to treating them with a compound of formula I.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

Preferred formula I compounds are those wherein:

$R_1$ is Br, or CN;

$R_2$ is optionally substituted benzyl;

$R_3$ is optionally substituted lower alkyl, optionally substituted phenyl, optionally substituted 2-thienyl, or optionally substituted 1-piperidinyl;

$R_4$ is hydrogen, or methyl;

$Z_1$ is CO, $SO_2$, or $SO_2N(R_5)$—;

$R_5$ is optionally substituted lower alkyl or optionally substituted phenyl; and n is 1.

More preferred formula I compounds for use in the methods and compositions for this invention are those wherein:

$R_1$ is CN;

$R_2$ is optionally substituted benzyl;

$R_3$ is optionally substituted lower alkyl, optionally substituted phenyl, optionally substituted 2-thienyl, or optionally substituted 1-piperidinyl;

$R_4$ is hydrogen, or methyl;

Z is CO, or $SO_2$; and n is 1.

Most preferred compounds of formula I for use in the present invention are those wherein:

$R_1$ is CN;

$R_2$ is benzyl;

$R_3$ is n-propyl, n-butyl, 3-methoxypropyl, 2-thienyl, 5-bromo-2-thienyl, phenyl, 4-methoxyphenyl, or 1-piperidinyl;

$R_4$ is hydrogen;

Z is $SO_2$; and n is 1.

Formula I compounds which are especially useful in the methods and compositions of the present invention include:

(R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile;

(R)-7-cyano-2,3,4,5-tetrahydro-1-(1H-imidazol-4-ylmethyl)-4-(1-oxobutyl)-3-(phenylmethyl)-1H-1,4-benzodiazepine;

(R)-4-[(5-bromo-2-thienyl)sulfonyl]-7-cyano-2,3,4,5-tetrahydro-1-(1H-imidazol-4-ylmethyl)-3-(phenylmethyl)-1H-1,4-benzodiazepine;

(R)-7-cyano-2,3,4,5-tetrahydro-1-(1H-imidazol-4-ylmethyl)-4-[(4-methoxyphenyl)sulfonyl]-3-(phenylmethyl)-1H-1,4-benzodiazepine;

(R)-7-cyano-2,3,4,5-tetrahydro-1-(1H-imidazol-4-ylmethyl)-3-(phenylmethyl)-4-(phenylsulfonyl)-1H-1,4-benzodiazepine;

(R)-7-cyano-2,3,4,5-tetrahydro-1-(1H-imidazol-4-ylmethyl)-3-(phenylmethyl)4-(propylsulfonyl)-1H-1,4-benzodiazepine;

(R)-4-(butylsulfonyl)-7-cyano-2,3,4,5-tetrahydro-1-(1H-imidazol-4-ylmethyl)-3-(phenylmethyl)-1H-1,4-benzodiazepine;

(R)-7-cyano-2,3,4,5-tetrahydro-1-(1H-imidazol-4-ylmethyl)-3-(phenylmethyl)-4-(1-piperidinylsulfonyl)-1H-1,4-benzodiazepine;

(R)-4-(3-methoxypropylsulfonyl)-7-cyano-2,3,4,5-tetrahydro-1-(1H-imidazol-4-ylmethyl)-3-(phenylmethyl)-1H-1,4-benzodiazepine; and pharmaceutically acceptable salts thereof.

The methanesulfonic acid salt of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile is particularly preferred for use in the methods and compositions of the present invention.

In a preferred embodiment of the present invention, the anti-proliferative cytotoxic agent is selected from the group consisting of paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0] heptadecane-5,9-dione and [1S-[1R*,3R*(E),7R*,10S*, 11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione, and the formula I compound is (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

In another preferred embodiment, the cytotoxic agent is paclitaxel and the formula I compound is (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

In another preferred embodiment of this invention, the cytotoxic agent is [1S-[1R*,3R*(E),7R*,10S*,11R*,12R*, 16S*]]-7,11-dihydroxy-8,8,10,12,16-pentamethyl-3-[1-methyl-2-(2-methyl-4-thiazolyl)ethenyl]4-aza-17-oxabicyclo-[14.1.0]heptadecane-5,9-dione and the formula I compound is (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

Methods employing a cytostatic agent selected from the group consisting of Iressa®, Herceptin®, Tamoxifen and surgical or chemical castration are particularly preferred for use in the combination methods of the invention.

When describing the compounds of the present invention, the phrase "lower alkyl" or "lower alk" (as part of another group) refers to an unsubstituted alkyl group of 1 to 6, preferably 1 to 4, carbon atoms.

The term "aralkyl" refers to an aryl group bonded directly through a lower alkyl group. A preferred aralkyl group is benzyl.

The term "aryl" refers to a monocyclic or bicyclic aromatic hydrocarbon group having 6 to 12 carbon atoms in the ring portion. Exemplary of aryl herein are phenyl, naphthyl and biphenyl groups.

The term "heterocyclo" refers to a fully saturated or unsaturated, aromatic or nonaromatic cyclic group which is a 4 to 7 membered monocyclic, 7 to 11 membered bicyclic, or 10 to 15 membered tricyclic ring system which has at least one heteroatom in at least one carbon atom-containing ring. Each ring of the heterocyclic group containing a heteroatom may have 1, 2, 3 or 4 heteroatoms selected from nitrogen, oxygen and sulfur where the nitrogen and sulfur heteroatoms may also optionally be oxidized and the nitrogen heteroatoms may also optionally be quaternized. The heterocyclo group may be attached at any heteroatom or carbon atom.

Exemplary monocyclic heterocyclo groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane, tetrahydro-1,1-dioxothienyl, dioxanyl, isothiazolidinyl, thietanyl, thiiranyl, triazinyl, triazolyl, and the like.

Exemplary bicyclic heterocyclo groups include benzothiazolyl, benzoxazolyl, benzothienyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

When a group is referred to as being optionally substituted, it may be substituted with one to five, preferably one to three, substituents such as F, Cl, Br, I, trifluoromethyl, trifluoromethoxy, hydroxy, lower alkoxy, cycloalkoxy, heterocyclooxy, oxo, lower alkanoyl, aryloxy, lower alkanoyloxy, amino, lower alkylamino, arylamino, aralkylamino, cycloalkylamino, heterocycloamino, disubstituted amines in which the two amino substituents independently are selected from lower alkyl, aryl or aralkyl, lower alkanoylamino, aroylamino, aralkanoylamino, substituted lower alkanoylamino, substituted arylamino, substituted aralkylanoylamino, thiol, lower alkylthio, arylthio, aralkylthio, cycloalkylthio, heterocyclothio, lower alkylthiono, arylthiono, aralkylthiono, lower alkylsulfonyl, arylsulfonyl, aralkylsulfonyl, sulfonamide (e.g., $SO_2NH_2$), substituted sulfonamide, nitro, cyano, carboxy, carbamyl (e.g., $CONH_2$), substituted carbamyl (e.g., CONH-lower alkyl, CON H-aryl, CONH-aralkyl or cases where there are two substituents on the nitrogen independently selected from lower alkyl, aryl or aralkyl), lower alkoxycarbonyl, aryl, substituted aryl, guanidino, and heterocyclos (e.g., indolyl, imidazolyl, furyl, thienyl, thiazolyl, pyrrolidyl, pyridyl, pyrimidyl and the like). Where noted above that the substitutuent is further substituted, it will be substituted with F, Cl, Br, I, optionally substituted lower alkyl, hydroxy, optionally substituted lower alkoxy, optionally substituted aryl, or optionally substituted aralkyl.

All stereoisomers of the formula I compounds of the instant invention are contemplated, either in admixture or in pure or substantially pure form. The definition of the formula I compounds embraces all possible stereoisomers and their mixtures. The formula I definition very particularly embraces the racemic forms and the isolated optical isomers having the specified activity.

The formula I compounds may be prepared by the procedures described in U.S. Pat. No. 6,011,029. All applications and patents referred to herein are hereby incorporated by reference.

The compounds of formula I are useful in various pharmaceutically acceptable salt forms. The term "pharmaceutically acceptable salt" refers to those salt forms which would be apparent to the pharmaceutical chemist, i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients or their pharmaceutically acceptable salts in combination with pharmaceutically acceptable carriers.

Pharmaceutically acceptable salts of the formula I compounds, cytotoxic agents and cytostatic agents which are suitable for use in the methods and compositions of the present invention include, but are not limited to, salts formed with a variety of organic and inorganic acids such as hydrogen chloride, hydroxymethane sulfonic acid, hydrogen bromide, methanesulfonic acid, sulfuric acid, acetic acid, trifluoroacetic acid, maleic acid, benzenesulfonic acid, toluenesulfonic acid, sulfamic acid, glycolic acid, stearic acid, lactic acid, malic acid, pamoic acid, sulfanilic acid, 2-acetoxybenzoic acid, fumaric acid, toluenesulfonic acid, methanesulfonic acid, ethanedisulfonic acid, oxalic acid, isethonic acid, and include various other pharmaceutically acceptable salts, such as, e.g., nitrates, phosphates, borates, tartrates, citrates, succinates, benzoates, ascorbates, salicylates, and the like. Cations such as quaternary ammonium ions are contemplated as pharmaceutically acceptable counterions for anionic moieties.

Preferred salts of formula I compounds include hydrochloride salts, methanesulfonic acid salts and trifluoroacetic acid salts with methanesulfonic acid salts being more preferred. In addition, pharmaceutically acceptable salts of the formula I compounds may be formed with alkali metals such as sodium, potassium and lithium; alkaline earth metals such as calcium and magnesium; organic bases such as dicyclohexylamine, tributylamine, and pyridine; and amino acids such as arginine, lysine and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The present invention also encompasses a pharmaceutical composition useful in the treatment of cancer, comprising the administration of a therapeutically effective amount of the combinations of this invention, with or without pharmaceutically acceptable carriers or diluents. The synergistic pharmaceutical compositions of this invention comprise an optional anti-proliferative cytotoxic agent or agents, an optional quiescence agent, a formula I compound, and a pharmaceutically acceptable carrier. The methods entail the use of a cytotoxic and/or a cytostatic agent in combination with a formula I compound. The compositions of the present invention may further comprise one or more pharmaceutically acceptable additional ingredient(s) such as alum, stabilizers, antimicrobial agents, buffers, coloring agents, flavoring agents, adjuvants, and the like. The antineoplastic agents, optional cytostatic agents (if chemical), formula I compounds and compositions of the present invention may be administered orally or parenterally including the intravenous, intramuscular, intraperitoneal, subcutaneous, rectal and topical routes of administration.

For oral use, the antineoplastic agents, cytostatic agents, formula I compounds and compositions of this invention may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added. In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic. In a preferred embodiment of the present invention, the formula I compounds or pharmaceutically acceptable salts thereof are formulated with a sulfobutylether-7-β-cyclodextrin or a 2-hydroxypropyl-β-cyclodextrin for intravenous administration.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration. Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The compounds of formula I, as well as the cytotoxic and cytostatic agents, described herein may also be delivered transdermally. The transdermal compositions can take the form of creams, lotions, aerosols and/or emulsions and can be included in a transdermal patch of the matrix or reservoir type as are conventional in the art for this purpose.

The combinations of the present invention may also be used in conjunction with other well known therapies that are selected for their particular usefulness against the condition that is being treated.

If formulated as a fixed dose, the active ingredients of the combination compositions of this invention are employed within the dosage ranges described below. Alternatively, the cytotoxic agents, cytostatic agents, and formula I compounds may be administered separately in the dosage ranges described below. In a preferred embodiment of the present invention, the antineoplastic agent is administered in the dosage range described below prior to administration of the formula I compound in the dosage range described below. Table I sets forth preferred chemotherapeutic combinations and exemplary dosages for use in the methods of the present invention. Where "Compound of Formula I" appears, any of the variations of Formula I set forth herein are contemplated for use in the chemotherapeutic combinations. Preferably, Compound 2 is employed.

| CHEMOTHERAPEUTIC COMBINATION | DOSAGE mg/m$^2$ (per dose) |
|---|---|
| Compound of Formula I | 2.5–750 mg/m2 |
| + Cisplatin | 5–150 mg/m2 |
| Compound of Formula I | 2.5–750 mg/m2 |
| + Carboplatin | 5–1000 mg/m2 |
| Compound of Formula I | 2.5–750 mg/m2 |
| + Radiation | 200–8000 cGy |
| Compound of Formula I | 2.5–750 mg/m2 |
| + CPT-11 | 5–400 mg/m2 |
| Compound of Formula I | 2.5–750 mg/m2 |
| + Paclitaxel | 40–250 mg/m2 |
| Compound of Formula I | 2.5–750 mg/m2 |
| + Paclitaxel | 40–250 mg/m2 |
| + Carboplatin | 5–1000 mg/m2 |
| Compound of Formula I | 2.5–750 mg/m2 |
| + 5FU and optionally | 5–5000 mg/m2 |
| + Leucovorin | 5–1000 mg/m2 |
| Compound of Formula I | 2.5–750 mg/m2 |
| + Epothilone | 1–500 mg/m2 |
| Compound of Formula I | 2.5–750 mg/m2 |
| + Gemcitabine | 100–3000 mg/m2 |
| Compound of Formula I | 2.5–750 mg/m2 |
| + UFT and optionally | 50–800 mg/m2 |
| + leucovorin | 5–1000 mg/m2 |
| Compound of Formula I | 2.5–750 mg/m2 |
| + Gemcitabine | 100–3000 mg/m2 |
| + Cisplatin | 5–150 mg/m2 |
| Compound of Formula I | 2.5–750 mg/m2 |
| + UFT | 50–800 mg/m2 |
| + Leucovorin | 5–1000 mg/m2 |
| Compound of Formula I | 2.5–750 mg/m2 |
| + Cisplatin | 5–150 mg/m2 |
| + paclitaxel | 40–250 mg/m2 |
| Compound of Formula I | 2.5–750 mg/m2 |
| + Cisplatin | 5–150 mg/m2 |
| + 5FU | 5–5000 mg/m2 |
| Compound of Formula I | 2.5–750 mg/m2 |
| + Oxaliplatin | 5–200 mg/m2 |
| + CPT-11 | 4–400 mg/m2 |
| Compound of Formula I | 2.5–750 mg/m2 |
| + 5FU | 5–5000 mg/m2 |
| + CPT-11 and optionally | 4–400 mg/m2 |
| + leucovorin | 5–1000 mg/m2 |
| Compound of Formula I | 2.5–750 mg/m2 |
| + 5FU | 5–5000 mg/m2 |
| + radiation | 200–8000 cGy |
| Compound of Formula I | 2.5–750 mg/m2 |
| + radiation | 200–8000 cGy |
| + 5FU | 5–5000 mg/m2 |
| + Cisplatin | 5–150 mg/m2 |
| Compound of Formula I | 2.5–750 mg/m2 |
| + Oxaliplatin | 5–200 mg/m2 |
| + 5FU and optionally | 5–5000 mg/m2 |
| + Leucovorin | 5–1000 mg/m2 |
| Compound of Formula I | 2.5–750 mg/m2 |
| + paclitaxel | 40–250 mg/m2 |
| + CPT-11 | 4–400 mg/m2 |
| Compound of Formula I | 2.5–750 mg/m2 |
| + paclitaxel | 40–250 mg/m2 |
| + 5-FU | 5–5000 mg/m2 |
| Compound of Formula I | 2.5–750 mg/m2 |
| + UFT | 50–800 mg/m2 |
| + CPT-11 and optionally | 4–400 mg/m2 |
| + leucovorin | 5–1000 mg/m2 |

In the above Table I, "5FU" denotes 5-fluorouracil, "Leucovorin" can be employed as leucovorin calcium, "UFT" is a 1:4 molar ratio of tegafur:uracil, and "Epothilone" is preferably a compound described in WO 99/02514 or WO 00/50423, both incorporated by reference herein in their entirety.

While Table I provides exemplary dosage ranges of the Formula I compounds and certain anticancer agents of the invention, when formulating the pharmaceutical compositions of the invention the clinician may utilize preferred dosages as warranted by the condition of the patient being treated. For example, Compound 2, a compound of Formula I, may preferably be administered at a dosage ranging from about 25–500 mg/m2 every three weeks for as long as treatment is required. Preferred dosages for cisplatin are about 75–120 mg/m2 administered every three weeks. Preferred dosages for carboplatin are within the range of about 200–600 mg/m2 or an AUC of about 0.5–8 mg/ml×min; most preferred is an AUC of about 4–6 mg/ml×min. When the method employed utilizes radiation, preferred dosages are within the range of about 200–6000 cGY. Preferred dosages for CPT-11 are within about 100–125 mg/m2, once a week. Preferred dosages for paclitaxel are about 130–225 mg/m2 every 21 days. Preferred dosages for gemcitabine are within the range of about 80–1500 mg/m2 administered weekly. Preferably UFT is used within a range of about 300–400 mg/m2 per day when combined with leucovorin administration. Preferred dosages for leucovorin are about 10–600 mg/m2 administered weekly.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

Certain cancers can be treated effectively with compounds of Formula I and a plurality of anticancer agents. Such triple and quadruple combinations can provide greater efficacy. When used in such triple and quadruple combinations the dosages set forth above can be utilized. Other such combinations in the above Table I can therefore include "Compound 2" in combination with (1) mitoxantrone+prednisone; (2) doxorubicin+taxane; or (3) herceptin+taxane. 5-FU can be replaced by UFT in any of the above combinations.

When employing the methods or compositions of the present invention, other agents used in the modulation of tumor growth or metastasis in a clinical setting, such as antiemetics, can also be administered as desired.

Clinical studies employing the combination chemotherapy methods of the invention may also be performed. Particularly preferred for such studies is the administration of about a 3 hour infusion of Taxol® (135 mg/m2) followed by about a 1 hour infusion of compound 2 (50 mg/m2) at three week intervals. In another protocol, Taxol® (80 mg/m2) is infused for about one hour followed by infusion of compound 2 (80 mg/m2). This protocol entails weekly administration. Another protocol entails the administration of a triple combination comprising about a 3 hour Taxol® infusion (135 mg/m2) followed by about a twenty minute carboplatin infusion (AUC=6), Taxol® and carboplatin being administered in this fashion every three weeks. In this protocol, compound 2 is administered to patients weekly in about a one hour infusion at 80 mg/m2.

The present invention encompasses a method for the synergistic treatment of cancer wherein a cytotoxic agent and/or cytostatic agent and a formula I compound are administered simultaneously or sequentially. Thus, while a pharmaceutical formulation comprising antineoplastic agent (s) and a formula I compound may be advantageous for administering the combination for one particular treatment, prior administration of the cytotoxic or cytostatic agent(s) may be advantageous in another treatment. It is also understood that the instant combination of antineoplastic agent(s) and formula I compound may be used in conjunction with other methods of treating cancer (preferably cancerous tumors) including, but not limited to, radiation therapy and surgery. It is further understood that the cytostatic agent, if any, may be administered sequentially or simultaneously with any or all of the other synergistic therapies.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent(s) or radiation) on the patient, and in view of the observed responses of the disease to the administered therapeutic agents.

In the methods of this invention, a compound of formula I is administered simultaneously or sequentially with a cytotoxic agent(s) and/or radiation and/or a cytostatic agent. Thus, it is not necessary that the chemotherapeutic agent(s) and compound of formula I, or the radiation and the compound of formula I, be administered simultaneously or essentially simultaneously. The advantage of a simultaneous or essentially simultaneous administration is well within the determination of the skilled clinician.

Also, in general, the compound of formula I, the optional cytostatic agent, and the optional cytotoxic agent(s) do not have to be administered in the same pharmaceutical composition, and may, because of different physical and chemical characteristics, have to be administered by different routes. For example, the compound of formula I may be administered orally to generate and maintain good blood levels thereof, while the chemotherapeutic agent(s) may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compound of formula I and cytotoxic agent(s) and/or radiation and/or cytostatic agent will depend upon the diagnosis of the attending physicians and their judgment of the condition of the patient and the appropriate treatment protocol. The compound of formula I and/or the cytotoxic agent(s) and/or cytostatic agent and/or radiation may be administered concurrently (e.g., simultaneously, essentially simultaneously or within the, same treatment protocol) or sequentially, depending upon the nature of the proliferative disease, the condition of the patient, and the actual choice of chemotherapeutic agent(s) and/or cytostatic agent and/or radiation to be administered in conjunction (i.e., within a single treatment protocol) with the compound of formula I.

If the compound of formula I and the cytotoxic agent(s) and/or radiation and/or cytostatic agent are not administered simultaneously or essentially simultaneously, then the initial order of administration of the compound of formula I, and the chemotherapeutic agent(s) and/or cytostatic agent and/or radiation, may be varied. Thus, for example, the compound of formula I may be administered first followed by the administration of the cytotoxic agent(s) and/or radiation; or the cytotoxic agent(s) and/or radiation may be administered first followed by the administration of the compound of formula I. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the cytostatic agent(s) and/or radiation may be administered initially, especially if a cytotoxic agent is employed. The treatment is then continued with the administration of the compound of formula I and optionally followed by administration of a cytostatic agent until the treatment protocol is complete.

Thus, in accordance with experience and knowledge, the practicing physician can modify each protocol for the administration of a component (therapeutic agent—i.e., compound of formula I, cytostatic agent, cytotoxic agent(s), or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

In order to facilitate a further understanding of the invention, the following examples are presented primarily for the purpose of illustrating more specific details thereof. The scope of the invention should not be deemed limited by the examples, but encompass the entire subject matter defined the claims.

Experimental Protocol

Compounds:

The following designations are used to identify the test compounds throughout the examples:

Compound 1: [1S-[1R*,3R*(E),7R*,10S*,11R*,12R*, 16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione Compound 2: (R)-2,3,4,5-tetrahydro-1-(1H-imidazol-4-ylmethyl)-3-(phenylmethyl)-4-(2-thienylsulfonyl)-1H-1, 4-benzodiazepine-7-carbonitrile, hydrochloride salt Compound 3: (R)-4-(butylsulfonyl)-7-cyano-2,3,4,5-tetrahydro-1-(1H-imidazol-4-yl methyl)-3-(phenylmethyl)-1H-1,4-benzodiazepine, hydrochloride salt Compound 4: (R)-4-(3-methoxypropylsulfonyl)-7-cyano-2, 3,4,5-tetrahydro-1-(1H-imidazol-4-ylmethyl)-3-(phenylmethyl)-1H-1,4-benzodiazepine, hydrochloride salt Compound 5: (R)-4-[(5-bromo-2-thienyl)sulfonyl]-7-cyano-2,3,4,5-tetrahydro-1-(1H-imidazol-4-ylmethyl)-3-(phenylmethyl)-1H-1,4-benzodiazepine, hydrochloride salt Compound 6: (R)-7-cyano-2,3,4,5-tetrahydro-1-(1H-imidazol-4-ylmethyl)-3-(phenylmethyl)-4-(1-piperidinylsulfonyl)-1H-1,4-benzodiazepine, hydrochloride salt Compound 7: (R)-7-cyano-2,3,4,5-tetrahydro-1-(1H-imidazol-4-ylmethyl)-4-[(4-methoxyphenyl)sulfonyl]-3-(phenylmethyl)-1H-1,4-benzodiazepine, hydrochloride salt Compound 8: 4-(3-bromophenylamino)-6,7-bis(methoxy) quinazoline Compound 9: N-[5-[[[5-(1,1-dimethylethyl)-2-oxazolyl] methyl]thio]-2-thiazolyl]-4-piperidinecarboxamide Drug Administration:

For administration of Compound 1 (an epothilone) to rodents, two different excipients have been used: (1) ethanol/water (1:9, v/v) and (2) Cremophor®/ethanol/water (1:1:8, v/v). Compound 1 was first dissolved in ethanol or a mixture of Cremophor®/ethanol (50:50). Final dilution to the required dosage strength is made less than 1 h before drug administration. For parenteral administration (IV), dilution was made with water so that the dosing solutions contain the specified excipient composition described above. For oral administration (PO), the dilution was made with 0.25 M sodium phosphate buffer (pH=8.0) at a ratio of 30/70, v/v. Paclitaxel was dissolved in a 50/50 mixture of ethanol and Cremophor® and stored at 4° C.; final dilution of paclitaxel was obtained immediately before drug administration with NaCl 0.9%. The volume of all compounds injected was 0.01 ml/g of mice, and 0.005 ml/g of rats.

Clonogenic Cell Colony-formation Assay:

The potency with which compounds kill clonogenic tumor cells (cells that are able to divide indefinitely to form a colony) in vitro was evaluated by the clonogenic assay. At the end of a 16 h drug exposure, monolayer cell cultures were dissociated by exposing the cells to 0.05% trypsin for 5 min at 37° C. Cells were resuspended in complete media (containing 10% FBS), counted with a Coulter Channelyzer, diluted and plated with 5 replicates per dilution, into plastic tissue culture petri dishes. The cells were incubated in a humidified atmosphere for 10 days at 37° C. Cell colonies were stained with crystal violet and those with >50 cells per colony were scored. The concentration required to kill clonogenic HCT-116 human colon carcinoma cells by 90% (i.e., the IC90) was determined.

BrdUrd Labeling of Asynchronously Growing Tumors:

BrdUrd was dissolved in sterile phosphate-buffered saline (PBS), pH 7.4, and administered by prolonged infusion (24 h) via the tail vein to mice at a dose of 100 mpk. Tumor-bearing mice were sacrificed at the end of the infusion period and the tumors excised for BrdUrd/DNA analysis.

Tumor Dispersal and Cell Staining:

Tumors were excised and minced with scissors, and were dissociated using an enzyme cocktail consisting of 0.025% collagenase (Sigma Chemical Co., St Louis, Mo.), 0.05% pronase (Calbiochem, LaJolla, Calif.) and 0.04% DNase (Sigma) for 1 h at 37° C. After removal of debris, by passing the cell suspensions through 70 μm nylon screens, the cells were washed in PBS, counted and resuspended in 75% methanol. The fixed cells were kept refrigerated at 4° C. until analysis.

On the day of assay, cells fixed in 75% methanol were washed once in PBS, resuspended in pepsin in 2N HCl (0.2 mg/ml) and incubated for 20 min at 37° C. Cells were then washed twice with 1 ml of PBS containing 0.5% fetal bovine serum (FBS) and 0.5% Tween 80. Following the two washes, cells were resuspended in 1 ml of PBS containing 2% FBS and incubated at room temperature for 20 min.

Cells were then spun down and the pellets were resuspended in 100 μl of anti-BrdUrd-FITC (10 μg/ml) (Boeringer Mannheim). Following an incubation period of 45 min, cells were washed in 1 ml of PBS containing 0.5% FBS and 0.5% Tween 80. Washed cells were resuspended in 1 ml of RNase (1 mg/ml) and incubated for 30 min at room temperature. Finally, propidium iodide (Sigma) was added at a concentration of 10 μg/ml in PBS.

In Vivo Antitumor Testing

The human tumor xenografts were maintained in Balb/c nu/nu nude mice. Tumors were propagated as subcutaneous transplants in the appropriate mouse strain using tumor fragments obtained from donor mice.

The required number of animals needed to detect a meaningful response (6–10) were pooled at the start of the experiment and each was given a subcutaneous implant of a tumor fragment (~50 mg) with a 13-gauge trocar. For treatment of early-stage tumors, the animals were again pooled before distribution to the various treatment and control groups. For treatment of animals with advanced-stage disease, tumors were allowed to grow to the pre-determined size window (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2−Wt1) provided a measure of treatment-related toxicity.

Tumor response was determined by measurement of tumors with a caliper twice a week until the tumors reached a predetermined "target" size of 0.5 or 1.0 g. Tumor weights (mg) were estimated from the formula:

Tumor weight=(length×width2)÷2

The maximum tolerated dose (MTD) is defined as the dose level immediately above which excessive toxicity (i.e. more than one death) occurred. The MTD was frequently equivalent to the optimal dose (OD). Activity is described at the OD. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Tumor response end-point was expressed in terms of tumor growth delay (T−C value), defined as the difference in time (days) required for the treated tumors (T) to reach a predetermined target size compared to those of the control group (C).

To estimate tumor cell kill, the tumor volume doubling time (TVDT) was first calculated with the formula:

TVDT=Median time (days) for control tumors to reach target size−Median time (days) for control tumors to reach half the target size And, Log cell kill (LCK)=T−C÷(3.32×TVDT)

A tumor is defined as "cured" when there is no detectable disease at the time of study termination (Day >75 days post-tumor implantation); the interval between study termination and the end of drug treatment always exceeded 10 times the volume doubling time of any particular tumor type.

Group sizes typically consisted of eight mice in all treatment and control groups. Statistical analyses of response data were carried out using the Gehan's generalized Wilcoxon test.

EXAMPLE 1

Tumors Comprise Both Proliferative and Non-proliferative Cell Populations

As a tumor grows, the vascular development often cannot keep pace with the rapid proliferation of the malignant cell population. Consequently, solid tumor masses typically exhibit abnormal blood vessel networks which, unlike vessels in normal tissues, fail to provide adequate nutritional support to the tumor cells for optimal growth. Solid tumors, therefore, comprise both proliferating and non-proliferating tumor cells. In most solid tumors, non-proliferating tumor cells constitute the majority of the total tumor cell population. Current anti-cancer agents target the biochemical processes of proliferating cells. Non-proliferating tumor cell populations and/or stationary cells are only minimally affected by such agents. Thus a major contributing factor to the failure of radiation or chemotherapy to cure neoplastic disease is the inability of these compounds to target the quiescent tumor cell population. In the HCT116 human colon carcinoma xenograft, using a prolonged (24 h) infusional BrdUrd regimen, it was estimated that the proliferating cell fraction in various tumors in vivo constitute only a minor fraction of the total cell population. In a 200–300 mg HCT-116 tumor only about 20% of the cell population contained proliferating cells while the remaining 80% contained non-proliferating cells (FIG. 1). A number of other tumors have also been examined and in each case non-proliferating cells constitute the majority of the cells present in the tumor (Table 2).

TABLE 2

| Tumor | Histology | Tumor Size (mg) | % Proliferating | % Non-proliferating |
|---|---|---|---|---|
| HCT116 | Colon ca. | 200–300 | 20 | 80 |
| San1 | Squamous cells ca. | 200–300 | 41 | 59 |
| MDA-Pca-2b | Prostate ca. | 200–300 | 35 | 65 |
| Pat-21 | Breast ca | 200–300 | 31 | 69 |
| San1 | Squamous cell ca. | 200–300 | 44 | 56 |

The nutrient-limited micro-environment of a solid tumor can be recapitulated in in vitro cell culture by controlling the growth condition of the culture media. Thus, by depleting nutrient supply (Day 8 culture) tumor cells can be induced into a non-proliferative or quiescent (stationary phase, about 90% non-proliferative) state, whereas under optimal nutrient condition (Day 3 culture), practically all tumor cells proliferate exponentially (log phase, about 90% proliferative).

EXAMPLE 2

The Compositions of the Invention Selectively Kill Non-proliferating Tumor Cells The potency with which Compound 2 kills clonogenic tumor cells (cells that are able to divide indefinitely to form a colony) in vitro was evaluated by the clonogenic assay. At the end of a 16 h drug exposure, monolayer cell cultures were dissociated by exposing the cells to 0.05% trypsin for 5 min at 37° C. Cells were resuspended in complete media (containing 10% FBS), counted with a Coulter Channelyzer, diluted and plated with 5 replicates per dilution, into plastic tissue culture petri dishes. The cells were incubated in a humidified atmosphere for 10 days at 37° C. Cell colonies were stained with crystal violet and those with >50 cells per colony were scored. The concentration needed to kill clonogenic HCT-116 human colon carcinoma cells by 90% (i.e., the IC90) was determined.

Figure 2:
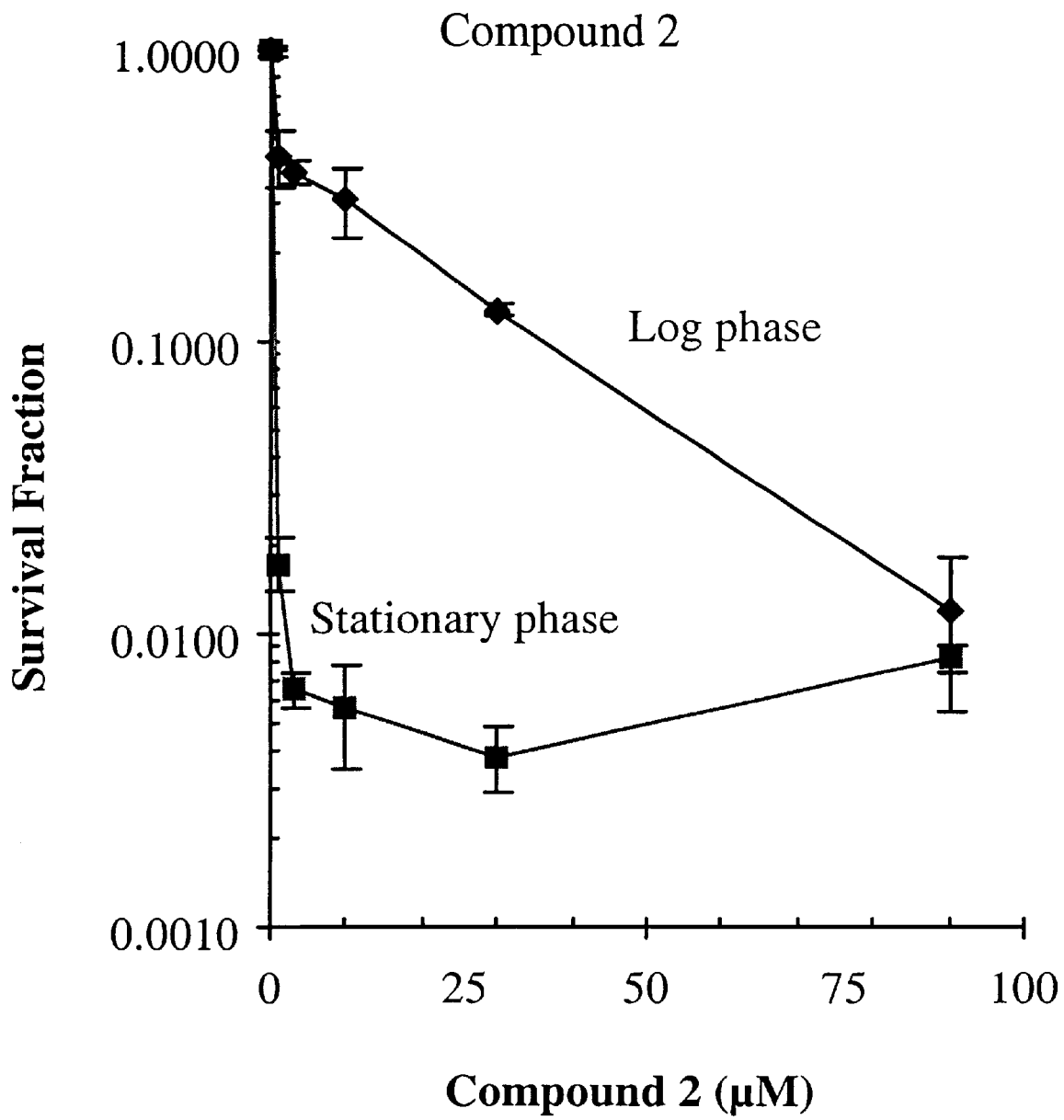
FIG. 2 illustrates selective targeting of non-proliferating HCT-116 tumor cells in vitro by Compound 2. Tumor cells in exponential growth (Day 2 nonconfluent and highly proliferative cells) were >44-fold less sensitive to Compound 2 (IC90=0.3 μM) than tumor cells in the stationary phase of growth (Day 8 highly confluent and non-proliferative cells).
Figure 3:
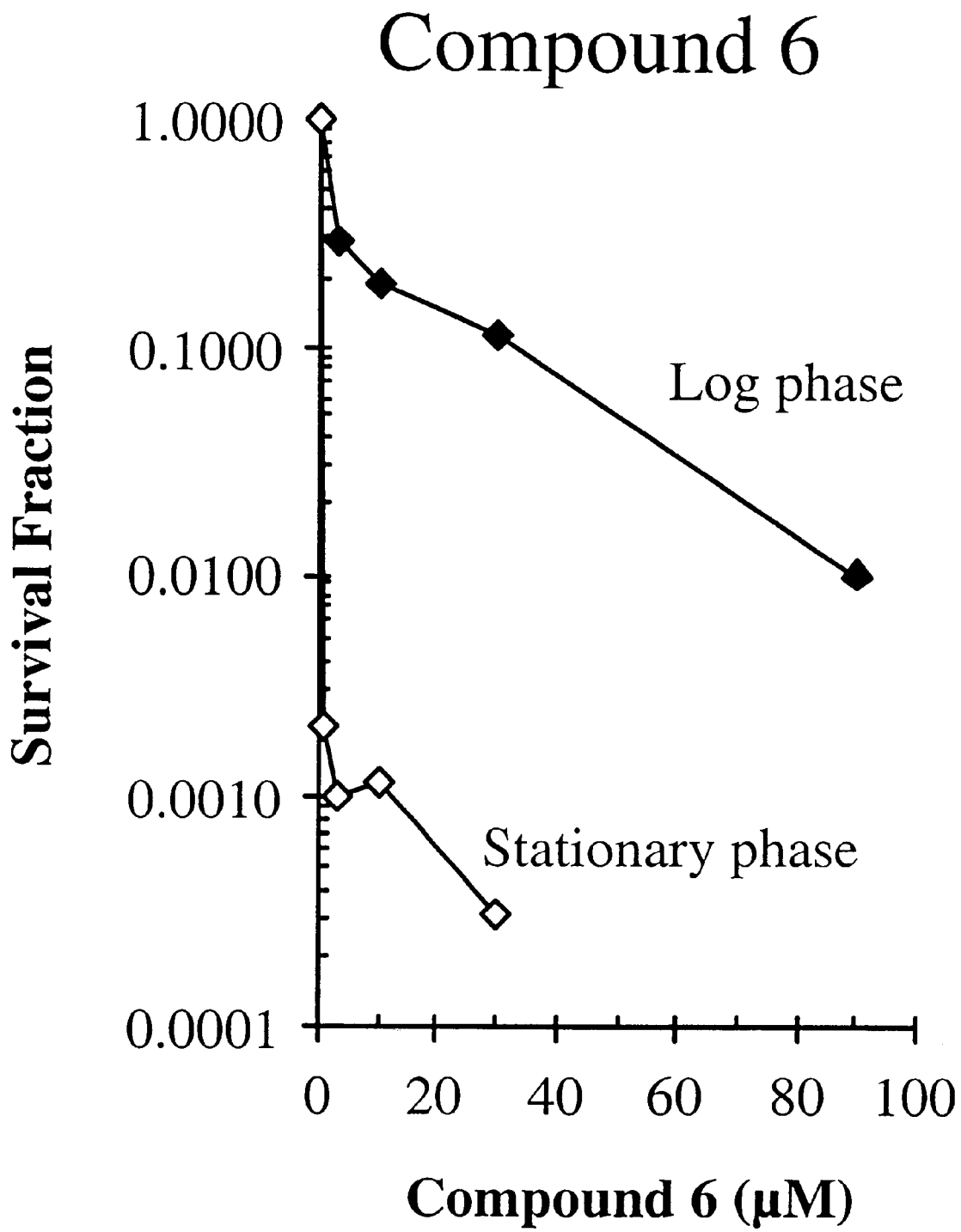
FIG. 3 illustrates selective targeting of non-proliferating HCT-116 tumor cells in vitro by Compound 6. Tumor cells in exponential growth (Day 2 nonconfluent and highly proliferative cells) were ~67-fold less sensitive to Compound 6 (IC90=1.04 μM) than tumor cells in stationary growth phase (Day 8 highly confluent and non-proliferative cells).
Figure 4:
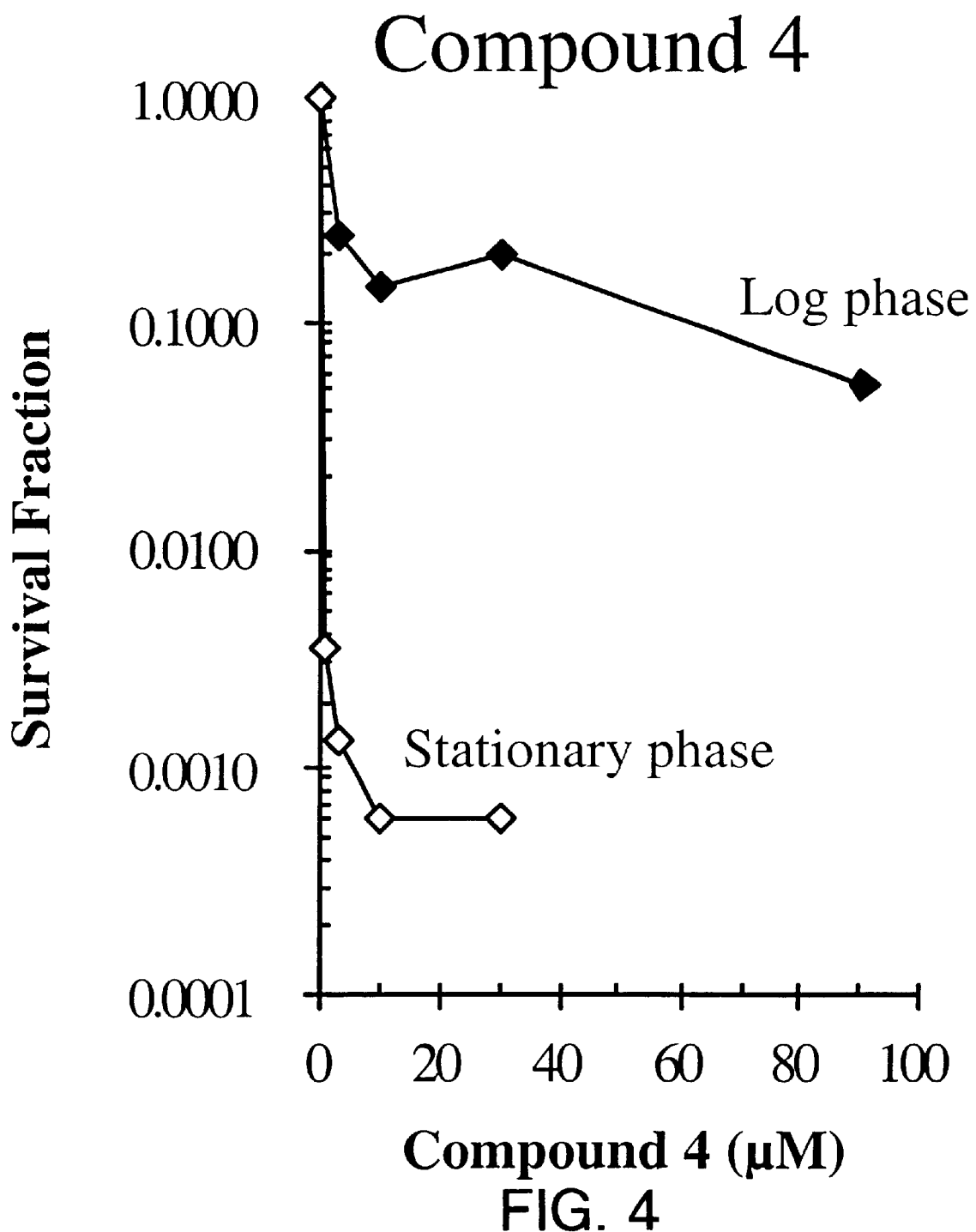
FIG. 4 illustrates selective targeting of non-proliferating HCT-116 tumor cells in vitro by Compound 4. Tumor cells in exponential growth (Day 2 nonconfluent and highly proliferative cells) were ~91.2-fold less sensitive to Compound 4 (IC90=1.05 μM) than tumor cells in stationary growth phase (Day 8 highly confluent and non-proliferative cells).

Compound 2 and analogues selectively kill non-proliferating (stationary) HCT116 human colon carcinoma cells as compared to proliferating (Log) cells (FIGS. 2–4 and Table 3). The degree (fold) differences in sensitivity between the proliferating and non-proliferating population ranged from 2.7–181.

TABLE 3

| Compound | $IC_{90}$ ($\mu$M) | | Non-proliferative cells selectivity |
|---|---|---|---|
| | Stationary | Log | ratio (fold) |
| Compound 3 | 0.36 | 65 | 181.0 |
| Compound 4 | 1.05 | 91.2 | 86.9 |
| Compound 5 | 1.08 | 84.7 | 78.4 |
| Compound 6 | 1.04 | 66.8 | 64.2 |
| Compound 2 | 0.96 | 36.7 | 44.2 |
| Compound 7 | 9.6 | 26 | 2.7 |

Figure 5:
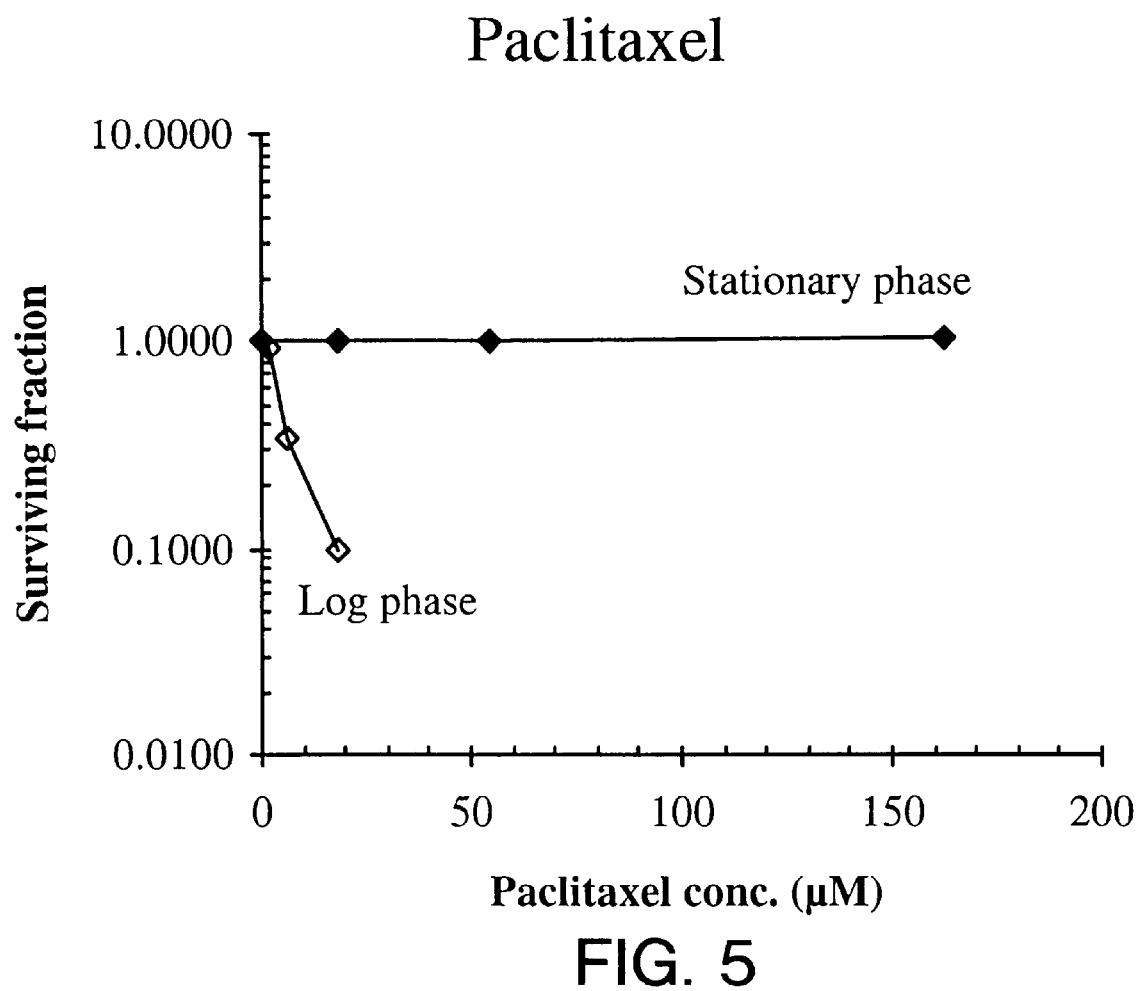
FIG. 5 illustrates that, unlike Compound 2 and its congeners, anti-proliferative agents such as paclitaxel selectively target proliferating HCT-116 tumor cells in vitro. Cancer cells in exponential growth (Day 2 nonconfluent and highly proliferative cells) were >>10-fold more sensitve to paclitaxel (IC90=17.8 nM) than tumor cells in stationary growth phase (Day 8 highly confluent and non-proliferative cells).
Figure 6:
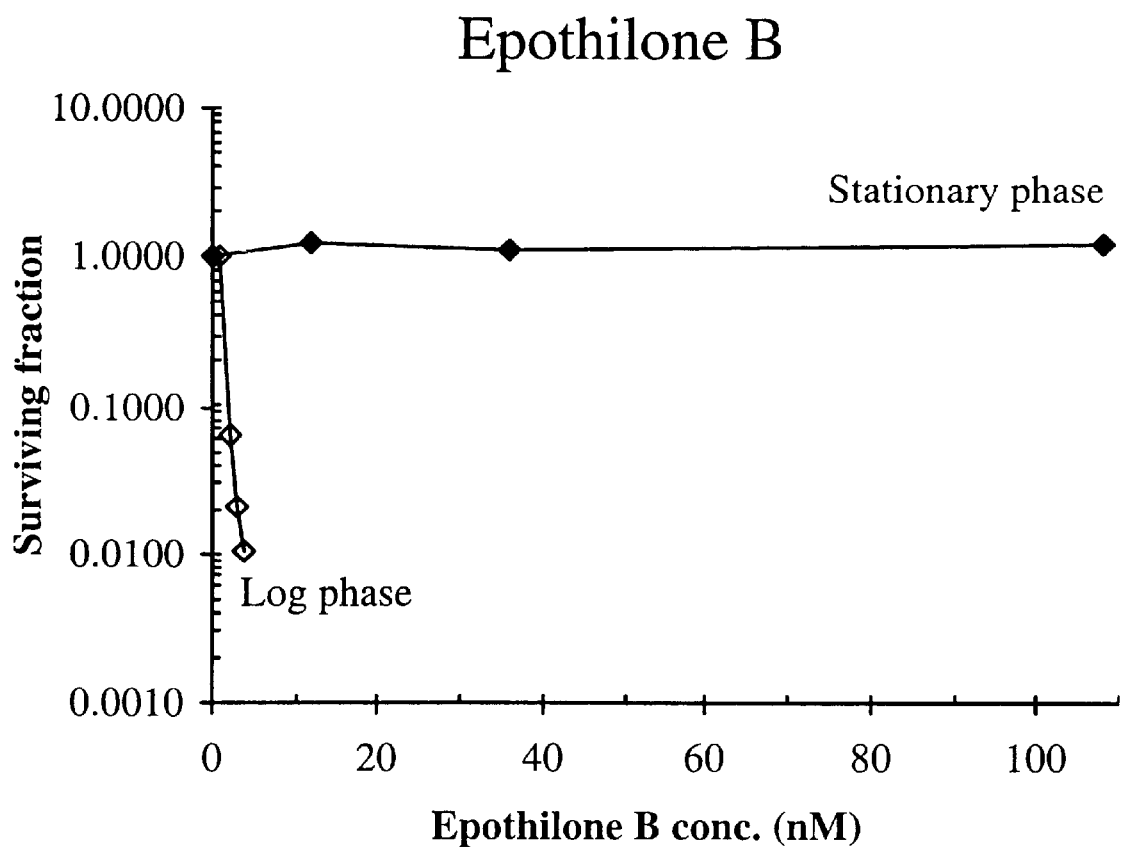
FIG. 6 illustrates that the epothilones, another class of antineoplastic, antiproliferative agents, selectively target proliferative cells. In this example, HCT116 cancer cells in exponential growth (Day 2 nonconfluent and highly proliferative cells) were >>83-fold more sensitive to epothilone B (IC90=1.3 nM) than HCT116 cells in stationary growth phase (Day 8 highly confluent and non-proliferative cells).

Most anticancer drugs work by affecting DNA synthesis or its function, and therefore target proliferating cells while leaving quiescent cells intact unless such cells divide soon after exposure to the drug. Consequently, the effectiveness of anticancer drugs is often limited by this refractory fraction of tumor cells. For example, in direct contrast to Compound 2, commonly used cancer agents such as paclitaxel, epothilone B and 5-flourouracil are preferentially cytotoxic to proliferating tumor cells and essentially ineffective against non-proliferating cells (FIGS. 5 and 6, and Table 4).

TABLE 4

| Compound | $IC_{90}$ ($\mu$M) | | Non-proliferative cells selectivity |
|---|---|---|---|
| | Stationary | Log | ratio (fold) |
| Paclitaxel | >162 nM | 17.8 nM | <0.1 |
| Epothilone B | >108 nM | 1.3 nM | <0.01 |
| 5-Fluorouracil | 4.6 $\mu$g/ml | >162 $\mu$g/ml | <0.03 |

EXAMPLE 3

Figure 7:
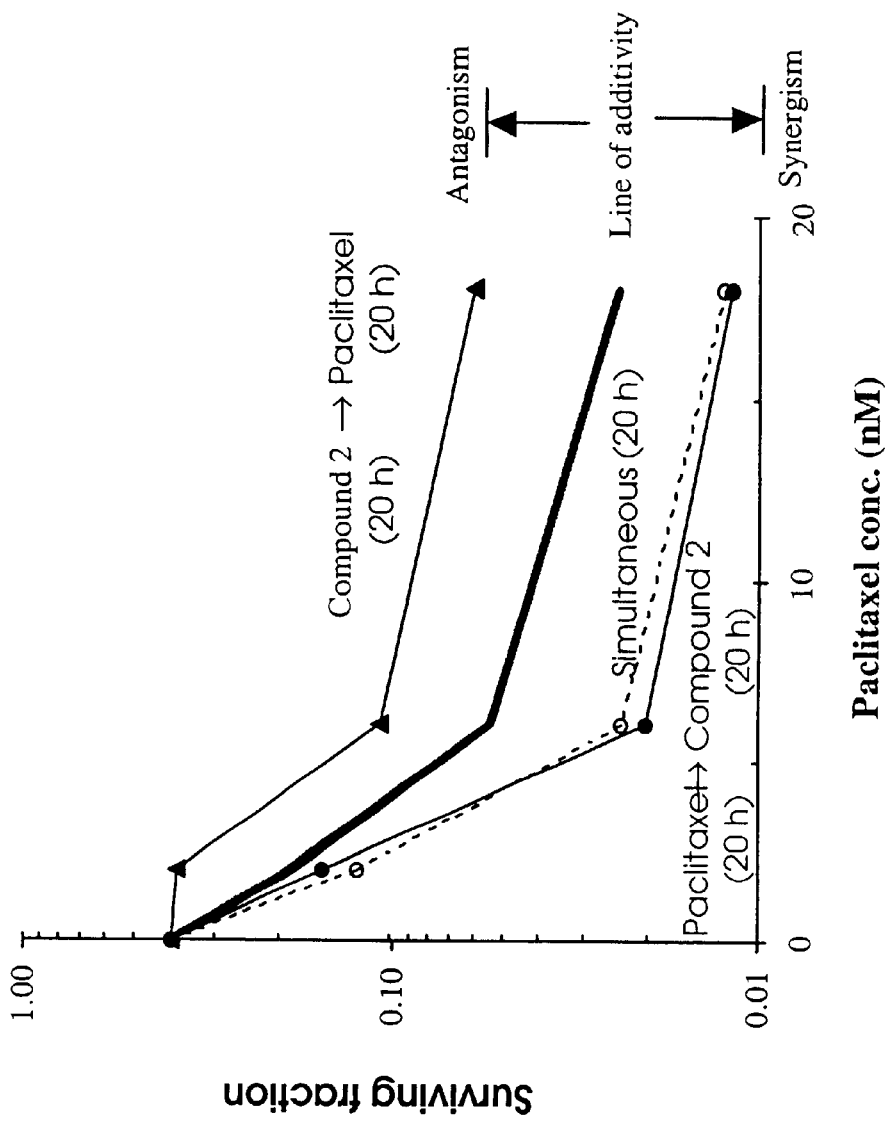
FIG. 7 shows the results of combination chemotherapy with Compound 2 and paclitaxel in the human colon carcinoma cell line, HCT116. These data demonstrate that the use of a combination treatment of Compound 2 and paclitaxel in the treatment of HCT116 cancer cells in vitro resulted in clearly synergistic anticancer activity. The sequence by which the two agents were given was shown to be important in determining whether synergism would result. Paclitaxel administered first for 20 hr followed by administration of Compound 2 (0.33 μM) for a second 20 hr period was clearly synergistic, as was simultaneous treatment with the two agents at the indicated concentrations for 20 hr. In contrast, the combination of Compound 2 (0.3 μM) followed by paclitaxel was found to be antagonistic.

Antiproliferative Agents in Combination with the Compounds of the Invention Act Synergistically to Kill Tumor Cells in vitro As discussed above, mechanistic studies strongly suggested that Compound 2 is selectively cytotoxic to non-proliferating tumor cells. This unique feature raises the prospect of synergistic combination therapy with existing anticancer drugs that primarily target proliferating tumor cells. For example, paclitaxel was highly cytotoxic to log phase HCT-116 cells in vitro yielding IC90 value of 17.8 nM (FIG. 5). However, against non-proliferating stationary cell population, it was completely non-toxic at concentrations as high as 162 nM (FIG. 5). A similar dramatic difference was observed with epothilone B (FIG. 6) with IC90 of 1.3 and >108 nM for proliferating and non-proliferating cells, respectively (Table 3). In vitro, combination of paclitaxel with Compound 2 yielded synergistic cytotoxicity such that the combination produced more than additive cell killing (FIG. 7). Moreover, it was discovered that in order to observe this synergistic combination, the two agents should be administered in a specific sequence. Synergism was observed when cells were treated with the two agents simultaneously or when paclitaxel preceded Compound 2. When Compound 2 was administered prior to paclitaxel by 24 hr, antagonism was observed.

Figure 8:
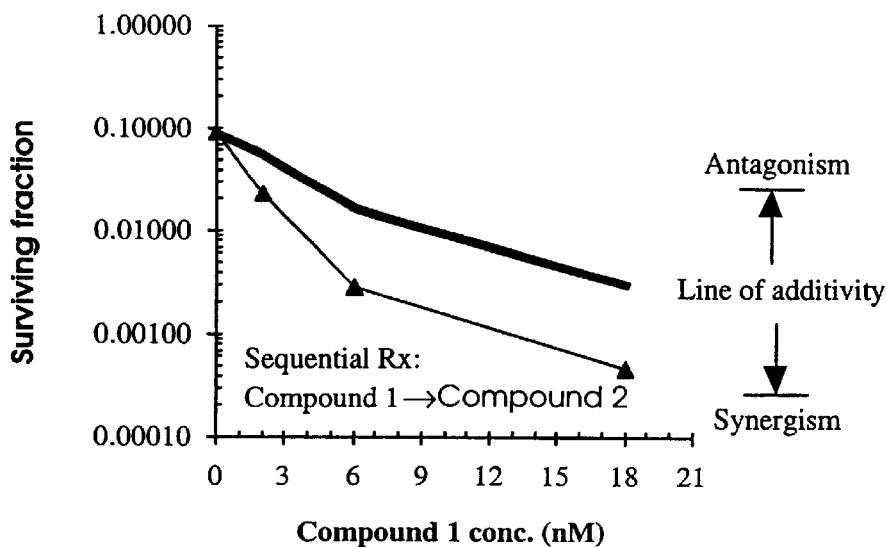
FIG. 8 shows the combination chemotherapy with Compound 2 and Compound 1 in the human colon carcinoma cell line HCT116. These data demonstrate that the use of a combination treatment of Compound 2 and Compound 1 in the treatment of HCT116 cancer cells in vitro resulted in clearly synergistic anticancer activity. Compound 1 was given first for 20 hr followed by Compound 2 (1 μM) for a second 20 hr period of treatment.
Figure 9:
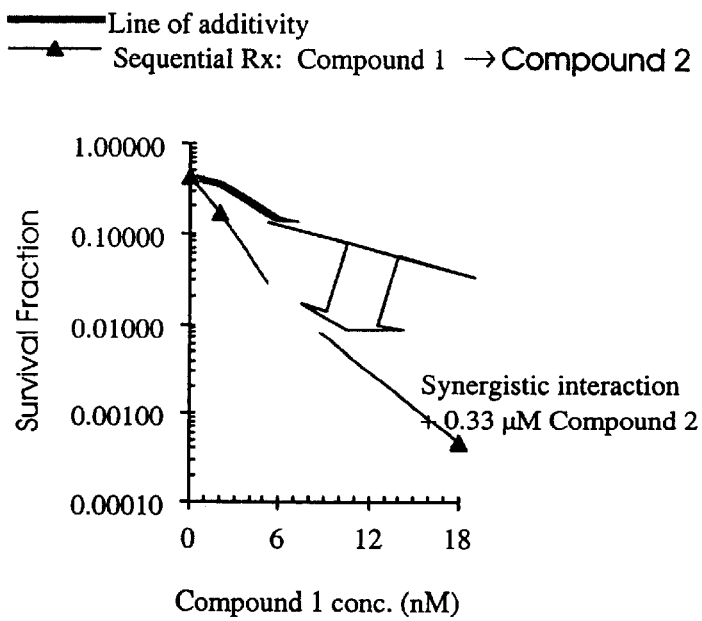
FIGS. 9 and 10 further illustrate the synergism with combination chemotherapy using Compound 2 and Compound 1. Synergism was obtained at a range of Compound 1 and Compound 2 concentrations and appeared not to be dependent on a particular concentration of each agent used in the combination. In the case of Compound 2, concentrations of 1 μM (FIG. 8), 0.33 μM (FIG. 9) and 0.11 μM (FIG. 10) all produced synergistic interaction with various concentrations of Compound 1. In these experiments, Compound 1 was given first for 20 hr followed by Compound 2 for a second 20 hr period of treatment.
Figure 10:
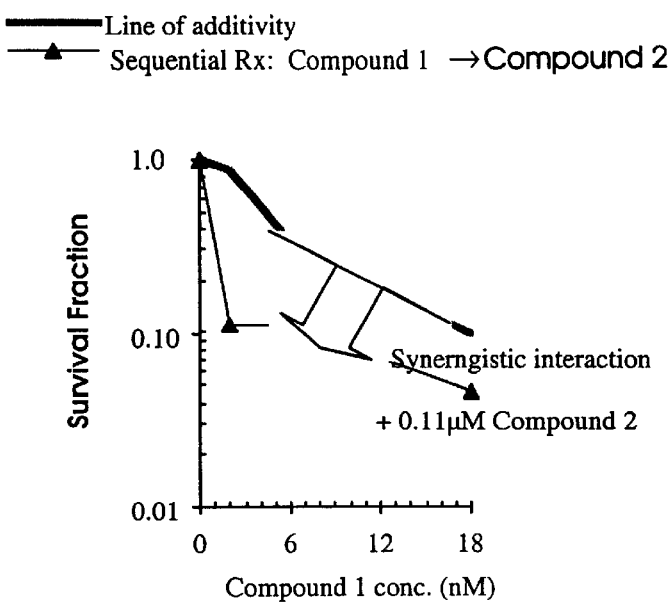

Similar synergism and sequence dependency were observed with a combination of Compound 2 and Compound 1 (FIGS. 8–10).

EXAMPLE 4

Figure 11:
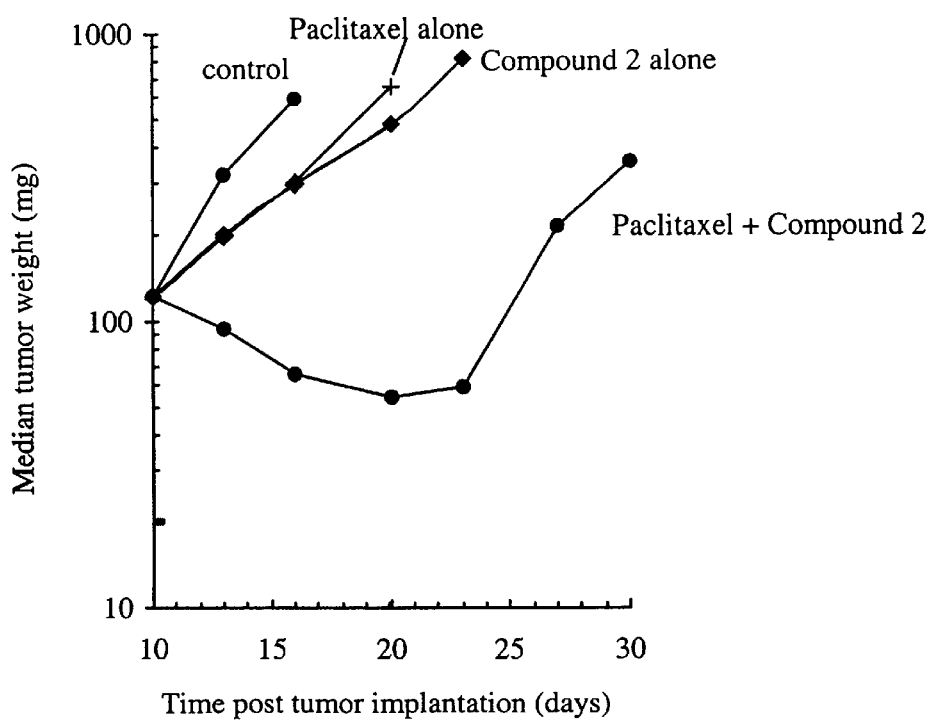
FIG. 11 demonstrates the synergism in vivo in human tumor xenografts (HCT116 human colon carcinoma) grown in nude mice obtained following combination chemotherapy using Compound 2 and paclitaxel. In this experiment, Compound 2 was given by prolonged iv infusion (24 hr) at a dose of 125 mg/kg. Paclitaxel was administered ip at a dose of 24 mg/kg at the end of the Compound 2 infusion period (considered simultaneous administration).

Anti-proliferative Agents in Combination with the Compounds of the Invention Act Synergistically to Kill Tumor Cells in Human Tumor Xenografts Combination therapy with infusional Compound 2 plus iv bolus paclitaxel was performed using the sc HCT-116 tumor model (FIG. 11). While the individual agents given alone were inactive (0.4 and 0.6 LCK for Compound 2 and paclitaxel, respectively), the combination (Compound 2, 125 mpk 24 h iv infusion plus paclitaxel, 24 mg/kg iv) yielded 1.8 LCK, a synergistic effect.

Figure 12:
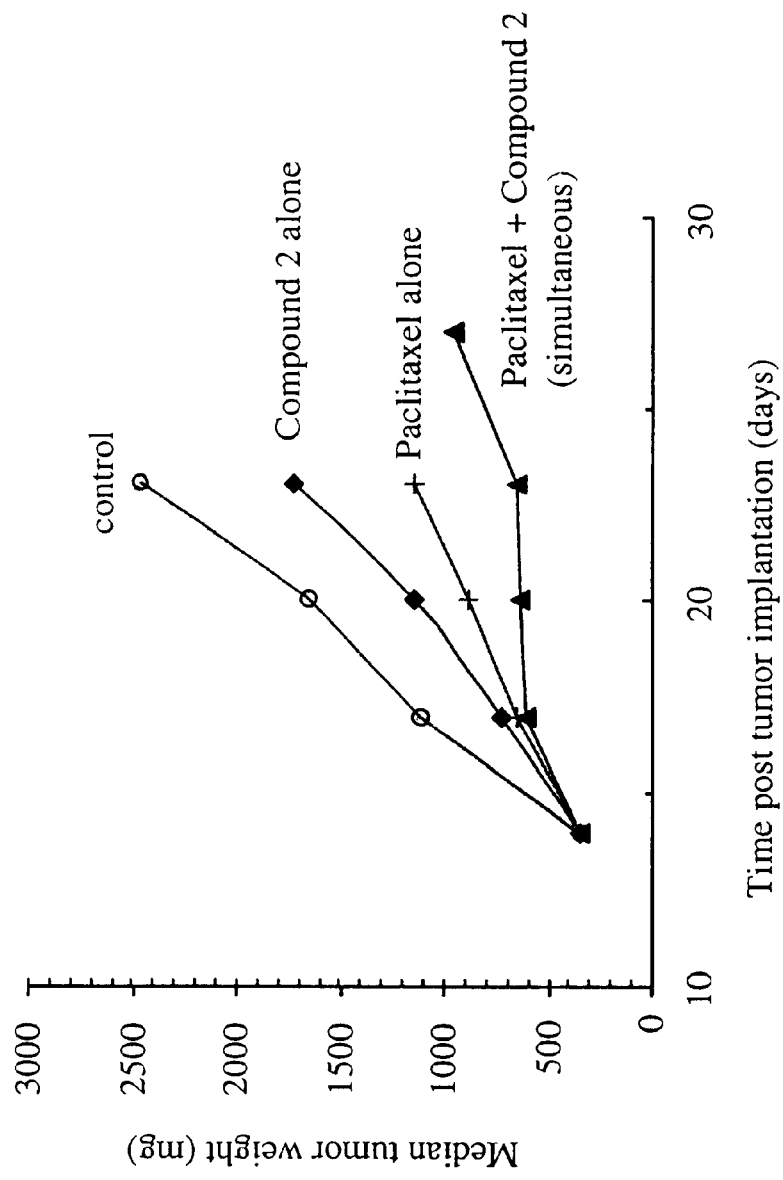
FIG. 12 demonstrates the synergism in vivo in a paclitaxel-resistant human tumor xenograft (Pat-7 human ovarian carcinoma) grown in nude mice following combination chemotherapy using Compound 2 and paclitaxel. Paclitaxel and Compound 2 were administered simultaneously; paclitaxel by iv route of administration and Compound 2 by ip route of administration. Data shown were maximum tolerated regimens: paclitaxel (36 mg/kg, iv, q3d×3); Compound 2 (350 mg/kg, ip, q3d×3).
Figure 13:
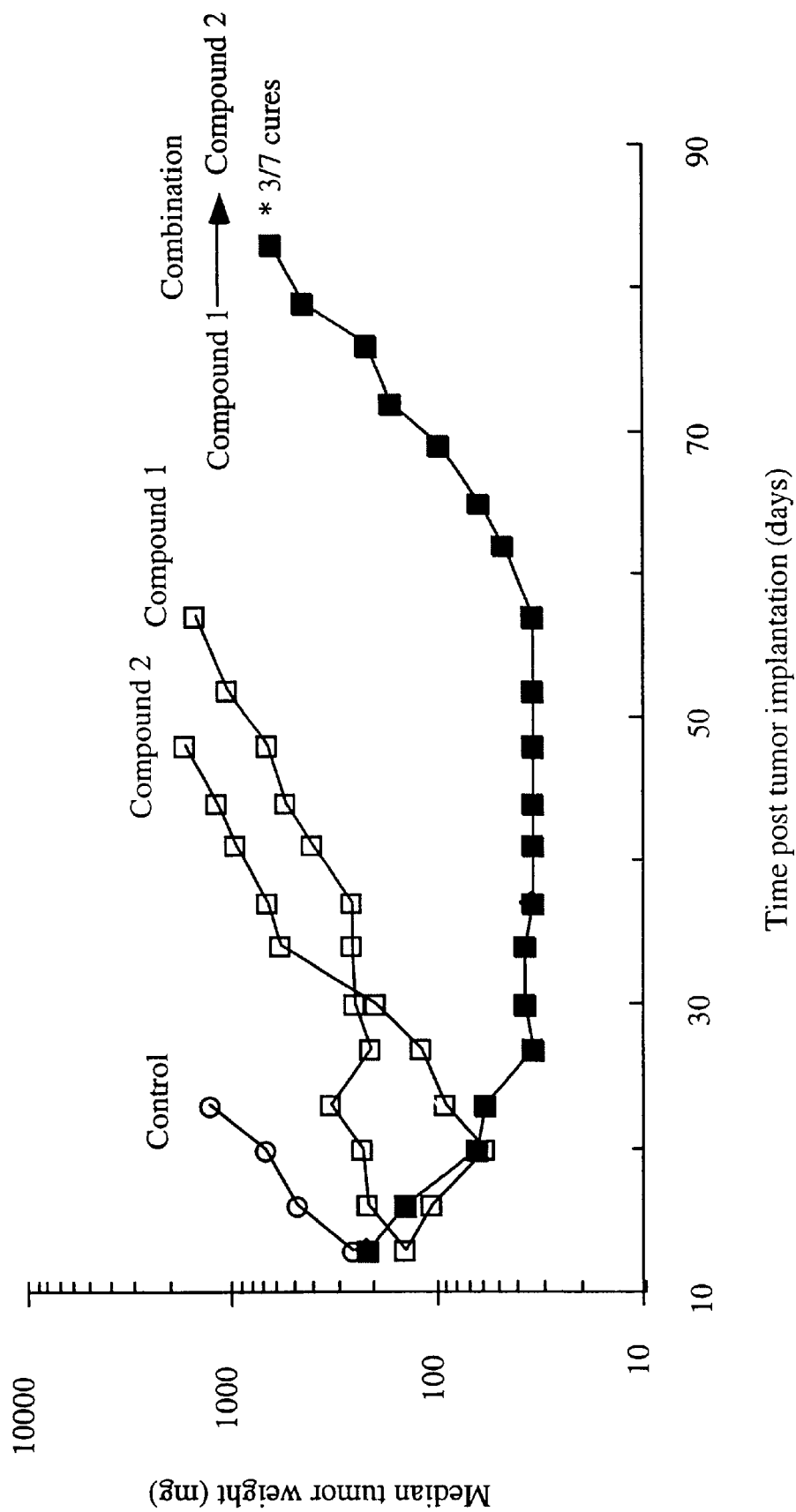
FIG. 13 demonstrates the therapeutic synergism in vivo in multidrug-resistant human tumor xenografts (HCTVM46 human colon carcinoma) grown in nude mice following combination chemotherapy using Compound 2 and Compound 1. Compound 1 was administered iv 24 hr preceding the administration Compound 2 ip. Data shown were maximum tolerated regimens: Compound 1 alone (15 mg/kg, q4d×3), Compound 2 alone (400 mg/kg, q4d×3), combination (Compound 1 at 6 mg/kg followed by Compound 2 at 400 mg/kg).

Combination chemotherapy with Compound 2 and paclitaxel given by bolus administration also demonstrated synergism in Pat-7 human ovarian carcinoma cells derived from a cancer patient who developed resistance to TAXOL®. Paclitaxel and Compound 2 given at their respective maximum tolerated doses, yielded less than 1 log cell kill (LCK) of tumor response in this resistant tumor model as single agent treatments. However, the combination of Compound 2 and paclitaxel at the maximum tolerated doses produced therapeutic synergism and significant antitumor activity of 1.7 LCK (FIG. 12). Synergistic antitumor activity was also observed in HCT116 human colon carcinoma xenografts (FIG. 13). Compound 2, at dose levels that yielded similar systemic exposure that was observed in human patients (20–80 $\mu$M.hr), was shown to synergize with the antitumor action of paclitaxel.

Therapeutic synergism was also clearly demonstrated with the combination of Compound 1 and Compound 2 in vivo in the multidrug resistant human colon carcinoma xenografts HCT/VM46. Both Compound 1 and Compound 2 have modest antitumor activity in this model as a single agent treatment (FIG. 13). Both agents caused greater than 1 LCK of tumor response (1.6 and 1.1 LCK, respectively) but did not induce tumor cure. However, when the two agents were administered in combination (Compound 1 followed 24 hr later with Compound 2), dramatic improvement in antitumor activity was observed. Notably, a highly significant increase in tumor growth delay (3.7 LCK) including enhanced curative effects were observed in 3 out of 7 mice (FIG. 13).

Figure 14:
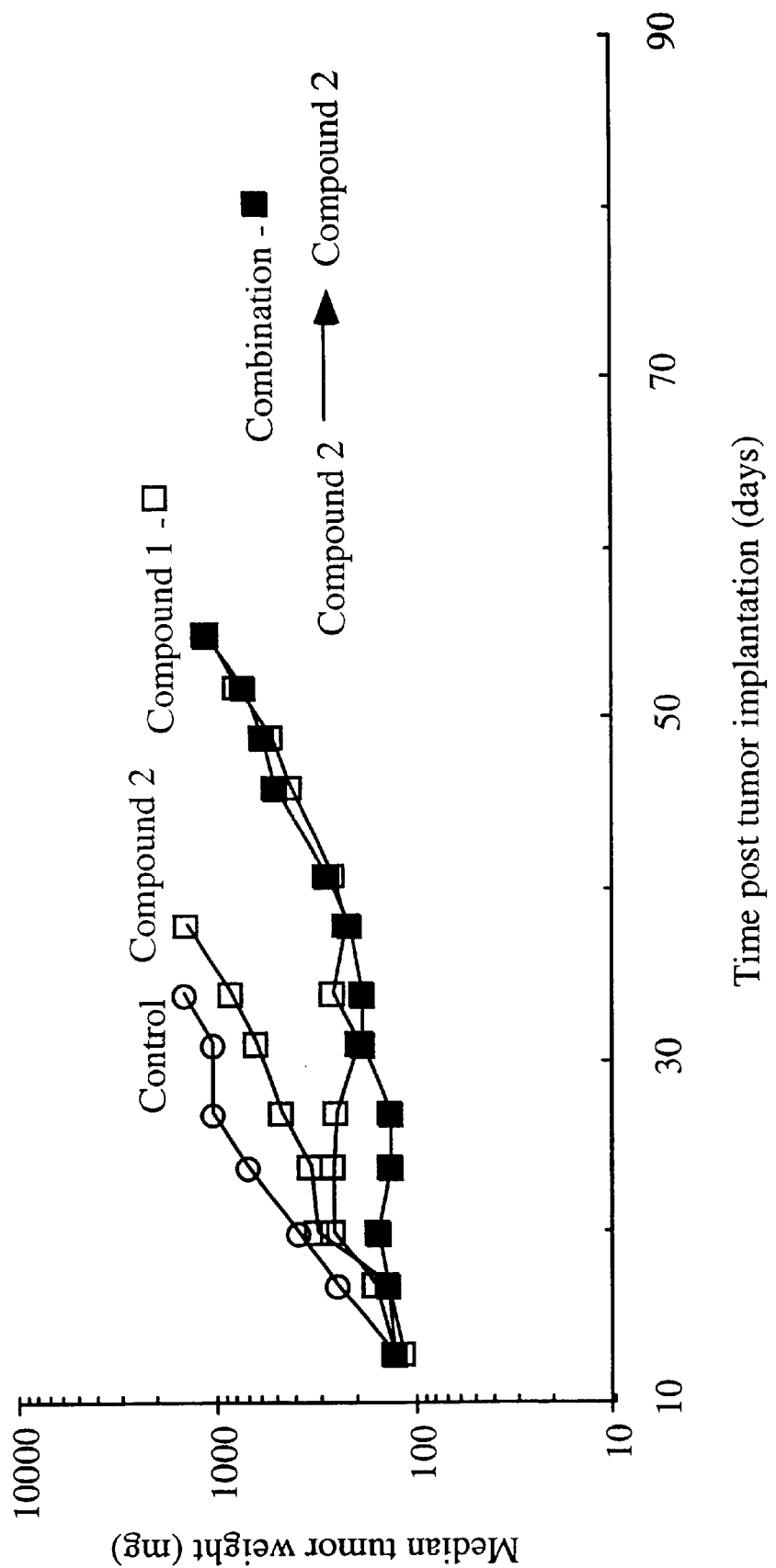
FIG. 14 demonstrates the schedule dependency of combining Compound 1 and Compound 2 in vivo against a multidrug-resistant human tumor xenografts (HCTVM46 human colon carcinoma) grown in nude mice. In contrast to other reported schedules described above, administration of Compound 2 one day before Compound 1 did not result in therapeutic synergism. Data shown were maximum tolerated regimens: Compound 1 alone (10 mg/kg, iv, q4d×3), Compound 2 alone (400 mg/kg, ip, q4d×3), combination (Compound 2 at 300 mg/kg followed by Compound 1 at 10 mg/kg).

The sequence dependency of the combination was demonstrated. When Compound 2 treatment was administered 24 h prior to Compound 1, no therapeutic synergism was observed (FIG. 14), with the combination performing only as well as Compound 1 given alone.

EXAMPLE 5

Compounds of the Invention Enhance the in vivo Antitumor Activity of the Topoisomerase I Inhibitor CPT-11 Versus Human Solid Carcinoma CPT-11 is an antiproliferative cytotoxic anticancer agent that interacts specifically with the enzyme topoisomerase I which relieves torsional strain in DNA by inducing reversible single-strand breaks. The cytotoxicity of CPT-11 is due to double-strand DNA damage produced during DNA synthesis when replication enzymes interact with the ternary complex formed by topoisomerase I-DNA, and either CPT-11 or its active metabolite SN-38. Thus, CPT-11 is targeted selectively against proliferating cells that undergo active DNA synthesis. We have demonstrated in this example that combined treatment of mice bearing advanced (300–500 mg) HCT116 human colon carcinoma xenograft with CPT-11 1 hour before Compound 2 produced synergistic antitumor activities that were far superior than each of the agents administered singly (FIGS. 15A and 15B). In this study, CPT-11 was administered IV at or near its MTD of 30 mg/kg/inj. Compound 2 was given at two different dose levels: 60 and 80 mg/kg/inj, IV. These doses of Compound 2 were chosen because they produced drug exposures that approximate clinically achievable exposure. As shown in FIGS. 15A and 15B, both dose levels of Compound 2 when combined with CPT-11 produced significantly greater antitumor activity than each of the agents given singly. Moreover, the combination produced significantly higher partial and complete tumor regression rates than single agents alone.

TABLE 5

Antitumor activity of combination chemotherapy with compound 2 and CPT-11 against advanced HCT116 human colon carcinoma

| Drug Treatment[1] | Dose (mg/kg/inj) | Tumor Response[2] | | |
|---|---|---|---|---|
| | | LCK[3] | PR (%)[4] | CR (%[5]) |
| CPT-11 | 30 | 1.5 | 50 | 0 |
| Compound 2 | 80 | 1.0 | 25 | 0 |
| | 60 | 0.6 | 0 | 0 |
| CPT-11 + Compound 2 | 30 + 80 | >3.0 | 100 | 88 |
| CPT-11 + Compound 2 | 30 + 60 | >3.0 | 100 | 62 |

[1]Drug treatment regimen were IV, Q2D × 5. CPT-22 was given 1 hour before Compound 2
[2]Tumors were in the range of 300–500 (median ~ 200 mg) at the time of treatment initiations
[3]LCK = Log cell kill
[4]PR = Partial response, a reduction in tumor size by 50% or more.
[5]CR = Complete response, defined as the eradication by treatment of all readily measureable tumors. A tumor is defined as immeasureable when it is less than 35 mg. A complete response differs from a cure in that microscopic or occult tumors may remain which may lead to subsequent tumor progression.

EXAMPLE 6

Figure 16A:
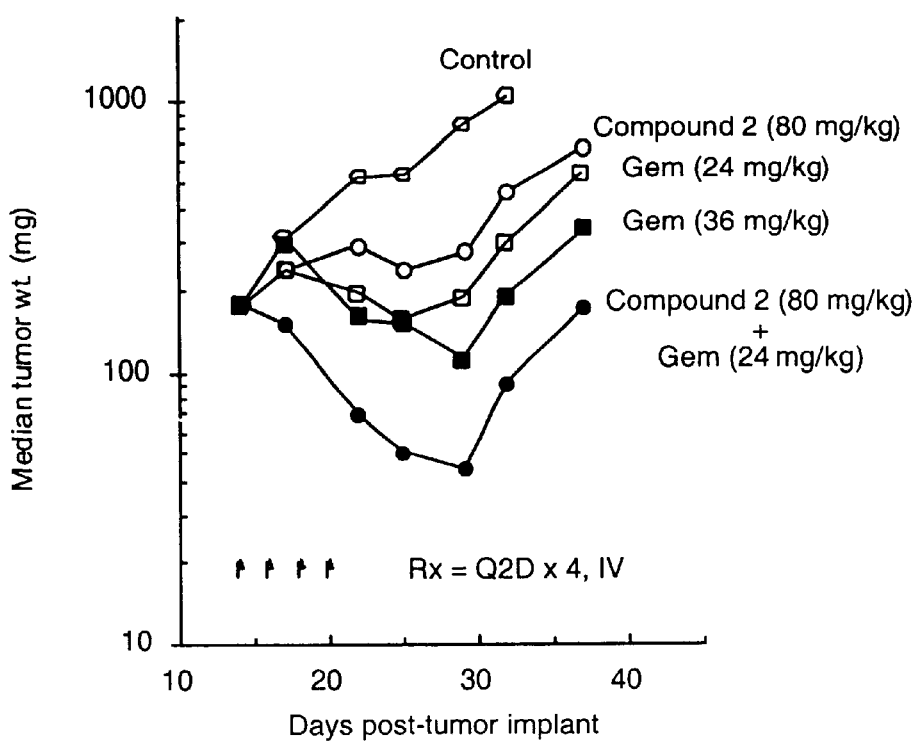
FIG. 16(A) demonstrates that combination chemotherapy with gemcitabine (Gem) plus Compound 2 elicits enhanced inhibition of tumor growth of the human colon carcinoma HT-29.
Figure 16B:
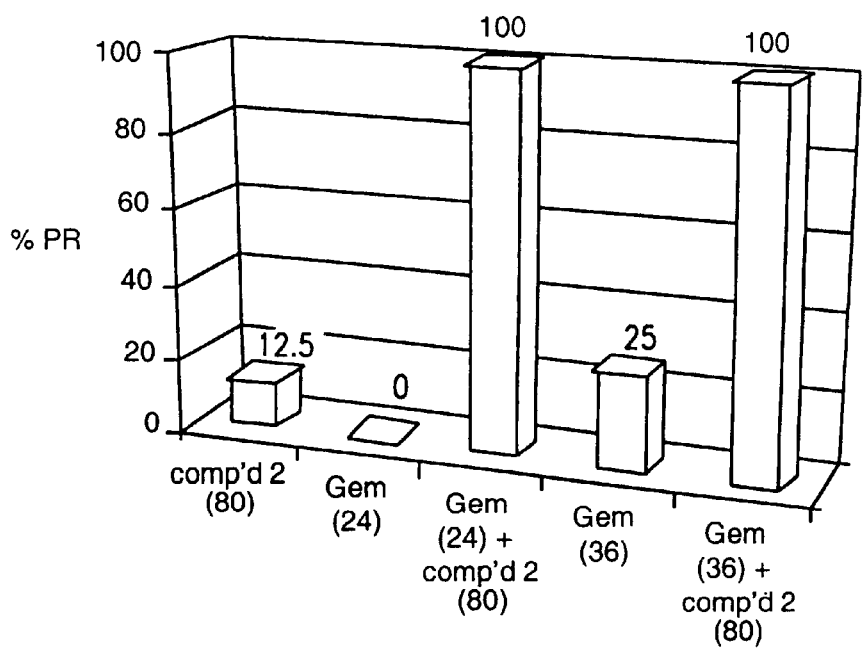
FIG. 16(B) demonstrates that the synergistic antitumor activity resulting from the combination of Gemcitabine and Compound 2 therapy also applied when tumor regression was used as an end-point of tumor response. Gem was administered 1 hour before Compound 2. Gem was administered IV at two dose levels, 24 and 36 mg/kg/inj, Q2D×4 (MTD=36 mg/kg/inj.). Compound 2 was given at two different dose levels: 60 and 80 mg/kg/inj, IV.

Compounds of the Invention Enhance the in vivo Antitumor Activity of Gemcitabine (GEMZAR) Versus Solid Human Tumors Gemcitabine is an antimetabolite type of antiproliferative cytotoxic chemotherapeutic agent that exhibits cell phase specificity. The agent primarily kills cells undergoing DNA synthesis (S-phase) and also blocks the progression of cells through the G1/S-phase boundary. Thus, gemcitabine is selectively toxic against cells that are actively dividing or proliferating. We have shown that the combination of gemcitabine with compound 2 (gemcitabine was administered 1 hour before Compound 2) produced enhanced antitumor activity against advanced HT-29 human colon carcinoma xenografts in nude mice (FIGS. 16A and 16B). Significantly, enhanced antitumor activity was observed not just in terms of growth delay (LCK) but more importantly, also resulted in pronounced improvement in response rate (tumor regression). Thus the combination of Compound 2 with Gemcitabine produced 100% PR in all treated mice while single agent compound 2 produced 12.5% PR and single agent gemcitabine produced 0 and 25% response rate respectively at 24 and 6 mg/kg/inj. dose (FIG. 16B).

EXAMPLE 7

Figure 17A:
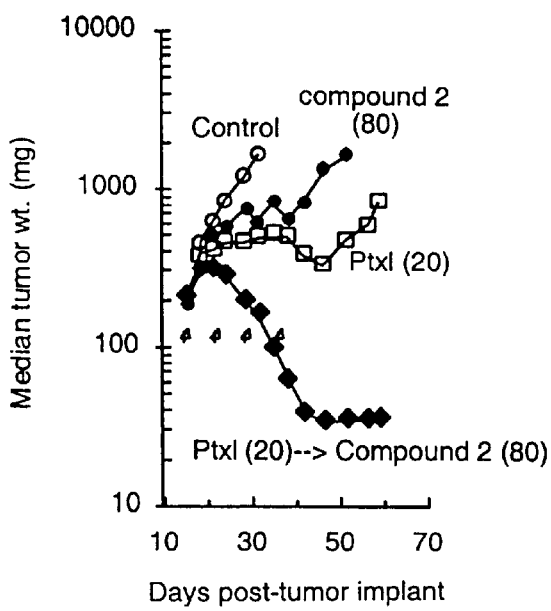
FIG. 17(A) demonstrates that combination chemotherapy with paclitaxel (Ptxl) plus Compound 2 elicited synergistic antitumor activity, in terms of tumor growth, against the human colon carcinoma HCT116.
Figure 17B:
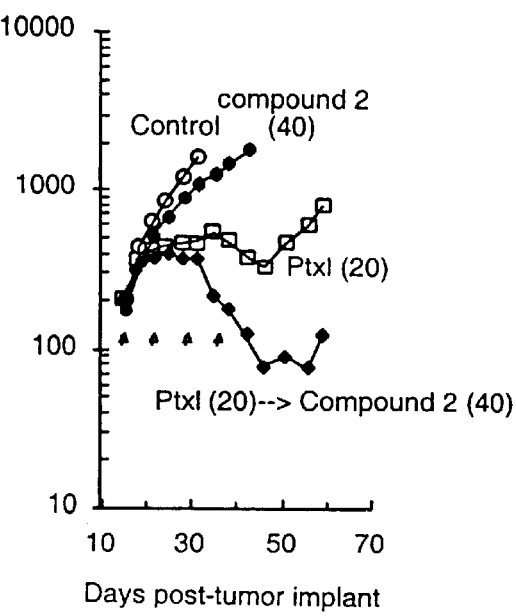
FIG. 17(B) demonstrates that the synergistic antitumor activity resulting from the combination of paclitaxel and Compound 2 therapy also applied when tumor regression and cure rate were used as end-points of tumor response. Paclitaxel was administered 3 hour before Compound 2. Paclitaxel was administered IV at 20 mg/kg/inj, Q7D×4. Compound 2 was given at two different dose levels: 40 and 80 mg/kg/inj, IV.
Figure 17C:
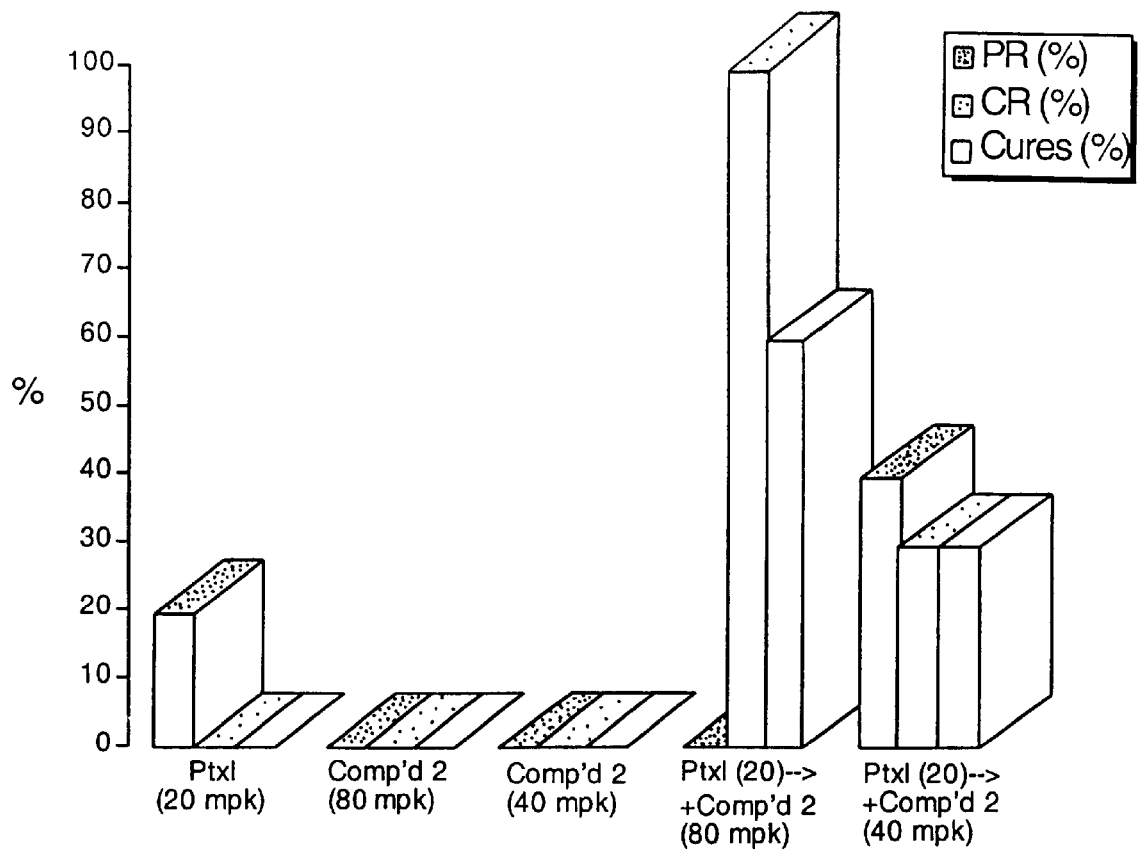
(FIG. 17(C)).

Paclitaxel in Combination with the Compounds of the Invention Acts Synergistically to Kill a Human Colon Cancer Xenograft Paclitaxel kills tumor cells as they enter the mitotic phase of the cell division cycle. Thus, paclitaxel is selectively toxic against proliferating cells (FIG. 5). We demonstrated that the combination of Compound 2 with paclitaxel produced synergistic antitumor activity against a human colon carinoma model, HCT116, in nude mice. FIGS. 17A and 17B show that iv administration of 40 or 80 mpk of Compound 2 three hours after iv administration of paclitaxel (20 mpk, weekly× 4) produced a dramatic enhancement of the antitumor effect of either agent alone; the extent of the therapeutic gain clearly exceeded that which would result if the two agents were merely exerting additive antitumor activity. This synergistic interaction can be seen not only on tumor growth delay, but also in terms of the more clinically relevant measures of tumor response, namely, partial and complete tumor regression (or response, PR and CR, respectively) and in tumor cures. This is illustrated in Table 6 and FIG. 17C.

TABLE 6

Antitumor of combination chemotherapy with compound 2 and paclitaxel versus advance HCT116 human colon carcinoma

| Drug Treatment[1] | Dose (mg/kg/inj) | Tumor Response[2] | | | |
|---|---|---|---|---|---|
| | | LCK[3] | PR (%)[4] | CR (%)[5] | Cures (%)[6] |
| Paclitaxel | 20 | 2.5 | 20 | 0 | 0 |
| Compound 2 | 80 | 1.1 | 0 | 0 | 0 |
| Compound 2 | 40 | 0.3 | 0 | 0 | 0 |
| Paclitaxel + compound 2 | 20 + 80 | >3.3 | 0 | 100 | 60 |
| Paclitaxel + compound 2 | 20 + 40 | >3.3 | 40 | 30 | 30 |

[1]Drug treatment regimen were IV, Q7D × 4. Paclitaxel was given 3 hour before Compound 2
[2]Tumors were in the range of 130–300 (median ~ 200 mg) at the time of treatment initiations
[3]LCK = Log cell kill
[4]PR = Partial response, a reduction in tumor size by 50% or more.
[5]CR = Complete response, defined as the eradication by treatment of all readily measureable tumors. A tumor is defined as immeasureable when it is less than 35 mg. A complete response differs from a cure in that microscopic or occult tumors may remain which may lead to subsequent tumor progression.
[6]Cure - no evidence of viable disease on Day 77 post-tumor implant as determined by autopsy.

EXAMPLE 8

Figure 18A:
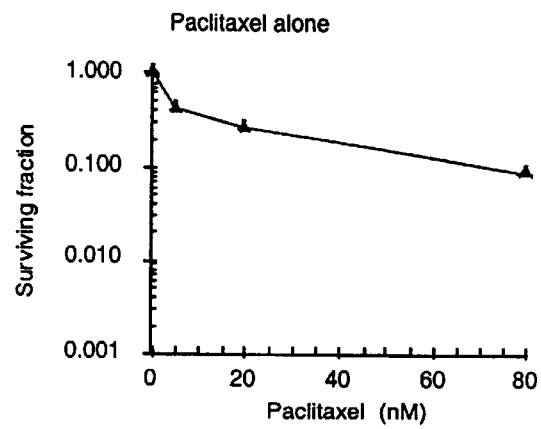
FIGS. 18A–18G show the anti-cancer effects of a variety of neoplastic agents used alone or in combination. The results show that Compound 2 and a Her-1 inhibitor, (Compound 8) when used in combination exert a synergistic cytotoxic effects in vitro against the Her-1 activated SAL-2 cancer cell line (Compare FIG. 18B with FIG. 18D).
Figure 18B:
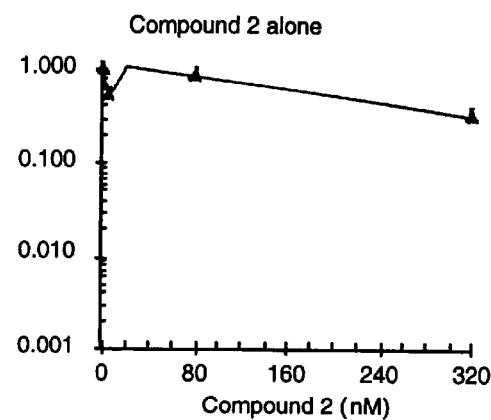
Figure 18C:
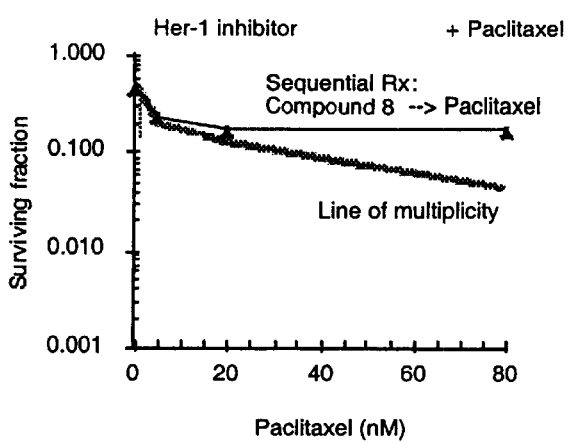
Figure 18D:
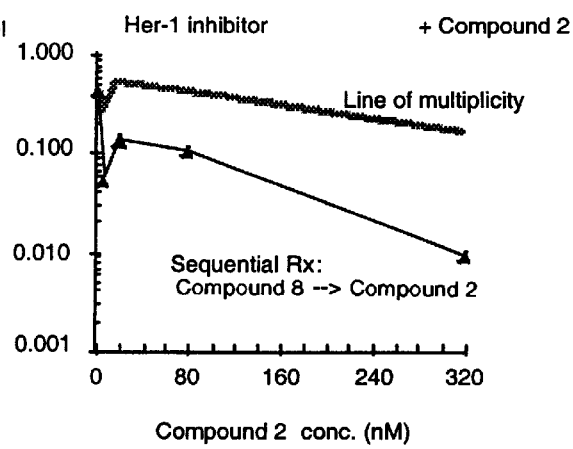

Her-1 Inhibitors (Compound 8) in Combination with the Compounds of the Invention Acted Synergistically to Kill SAL-2 Cancer Cells in vitro and the A431 Squamous Cell Carcinoma in vivo The epidermal growth factor (EGF, or Her-1) receptor has been implicated in many human epithelial and squamous cell carcinomas. The binding of EGF to its receptors in tumor cells leads to activation of protein tyrosine kinase activiity and tyrosine autophosphorylation. These events in turn lead to activation of a cascade of biochemical responses that are involved in the mitogenic (proliferative) signal transduction of cancer cells. Inhibition of EGF receptor binding have been shown in sensitive cells to lead to inhibition of cellular proliferation, cell cycle arrest and apoptosis. Thus, EGF or Her-1 inhibitors selectively target proliferating cells, and by interfering with mitogenic signal transduction, render cancer cells non-proliferative. Given the selectivity of the compounds of the present invention which target non-proliferative cells, we propose the concept that we can take advantage of this particular mode of action of Her-1 inhibitors, which by driving cancer cells into a non-proliferative state would "sensitize" them to the pro-apoptotic activity of compounds 2 and similar compounds in this invention. This hypothesis was proven true under both in vitro and in vivo experimental conditions. For in vitro, in order to assess the therapeutic efficacy of combining a Her-1 inhibitor with compound 2, experiments were performed utilizing the SAL-2 tumor cells which constitutively over-express the activated form of Her-I receptors. For this purpose, a Her-1 inhibitor, Compound 8, was used. As a reference, paclitaxel was used as an example of agents that target only proliferating cells and, according to our hypothesis, would not work well in the present experimental conditions, i.e. sequential drug exposure: Her-1 inhibitor first to induce cell stasis, followed by Compound 2 or paclitaxel. The data reveal that exponentially growing SAL2 cancer cells were relatively resistant to Compound 2 and paclitaxel when each was administered as a single agent, as shown in FIGS. 18A–18G. Sequential combination of Her-1 inhibitor '832 followed by paclitaxel was antagonistic as predicted by our hypothesis (FIG. 18C). By contrast, the sequential combination of Her-1 inhibitor (Compound 8) followed by Compound 2 was synergistic (FIG. 18D).

Figure 18E:
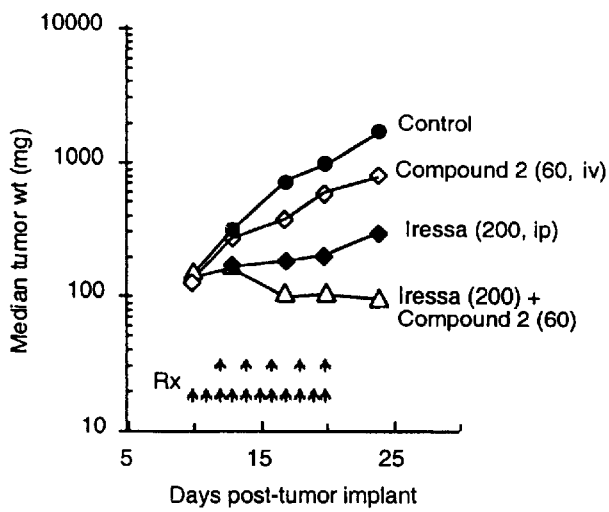
Figure 18F:
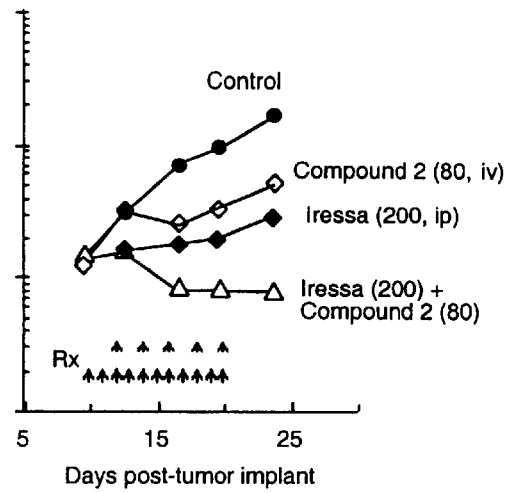
Figure 18G:
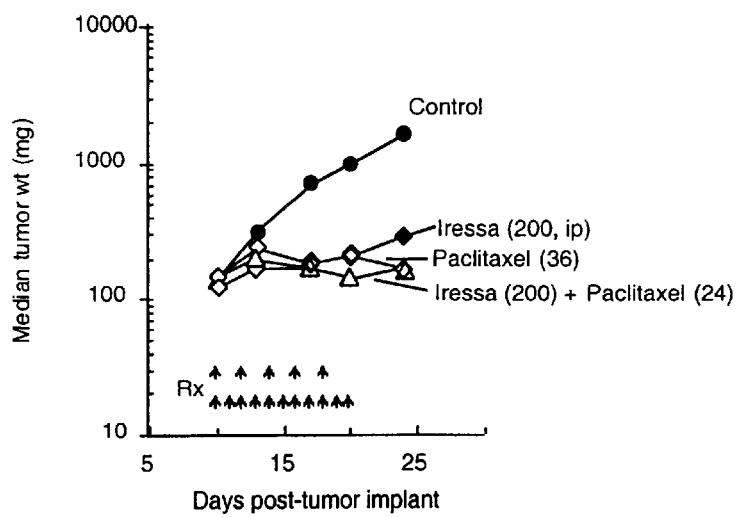

For demonstration of the effects of combining a Her-1 inhibitor with the Compounds of the present invention in vivo, we employed the Her-1 inhibitor Iressa® in combination with Compound 2 against the human squamous cell carcinoma, A431, known to overexpress the Her-1 receptor. As shown in FIGS. 18E and F, two separate dose levels of Compound 2 when used in combination with Iressa®, produced enhanced antitumor activity when compared each of the agents given alone. It should be noted that Iressa was administered on a daily treatment regimen, Q1D×11, the treatment of which was initiated 3 days prior to treatment initiation with Compound 2. Compound 2 was administered on a Q2D×5 schedule. Importantly, this regimen of sequential drug treatment (i.e.Iressa® first) worked poorly with paclitaxel (FIG. 18G). The combination of Iressa® and paclitaxel produced antitumor effects that were no better than either of the single agents used alone.

EXAMPLE 9

Figure 19:
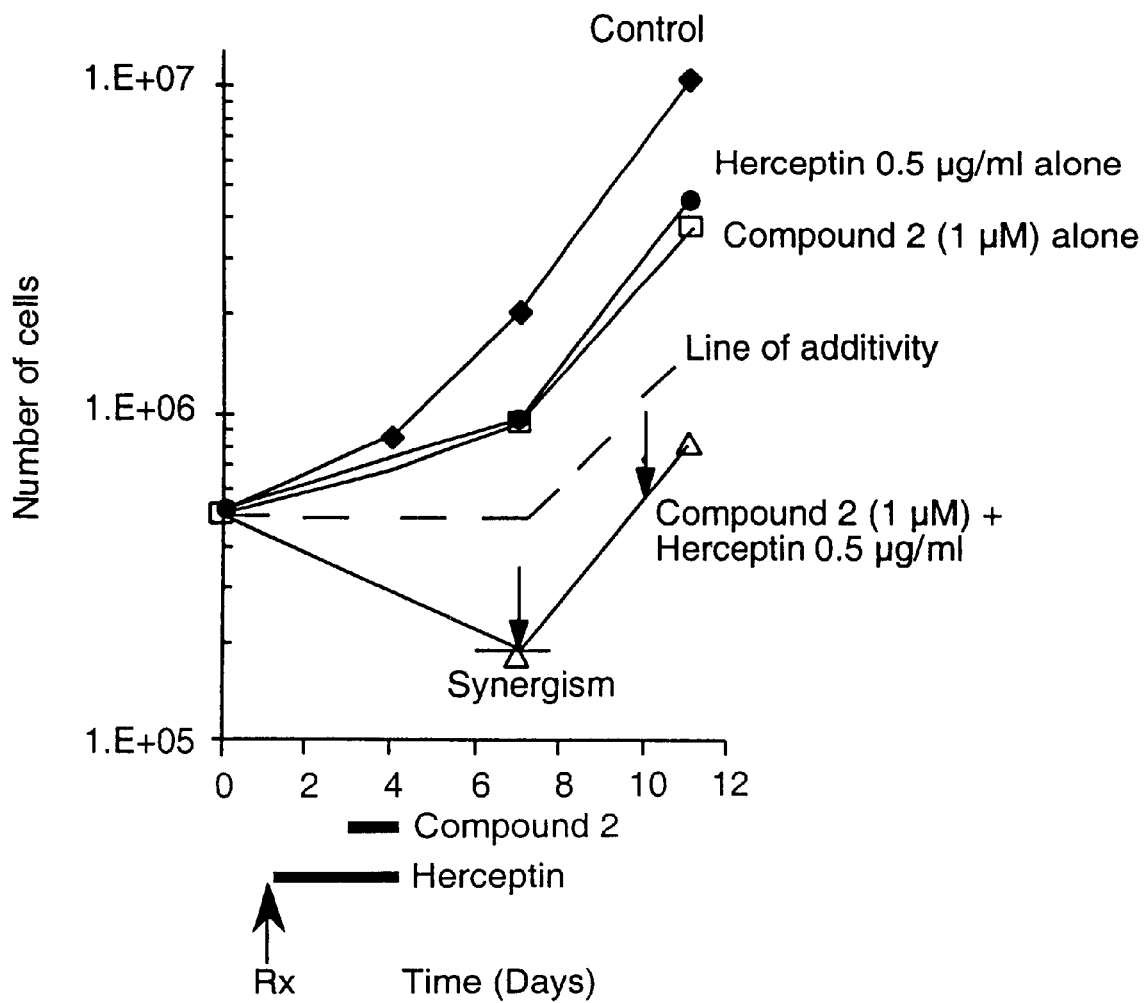
FIG. 19 demonstrates that combined treatment with Compound 2 and Herceptin yielded synergistic antiproliferative activity against the BT474 human breast carcinoma cell line. Herceptin® treatment was initiated 2 days before Compound 2 as illustrated in the figure.

Combination of Compound 2 with Her-2 Directed Antibody Herceptin Produced Synergistic Inhibitory Effects on the Growth of Her-2 Overexpressing Human Breast Cancer Cells HER-2 (or c-erbB2) proto-oncogene encodes a transmembrane receptor protein of 185 kDa, which is structurally related to the epidermal growth factor receptor, or Her-1. HER2 protein overexpression is observed in 25%-30% of primary breast cancers. Herceptin® is a recombinant DNA-derived humanized monoclonal antibody that selectively binds to the extracellular domain of the Her-2 protein. Herceptin® has been shown, in both in vitro assays and in animals, to inhibit the proliferation of human tumor cells that overexpress Her-2. Thus, according to the concept proposed in this invention, Herceptin® is an example of a class of agents which act by rendering cancer cells non-proliferative, thereby sensitizing tumor cells to the anticancer action of compounds of the present invention, which selectively target non-proliferating cells. Thus, in this example, pretreatment of the human breast cancer cell line BT-474, which overexpresses Her-2, for 2 days prior to treatment with Compound 2 produced synergistic antiproliferative effects on cancer cell growth (FIG. 19).

EXAMPLE 10

Figure 20:
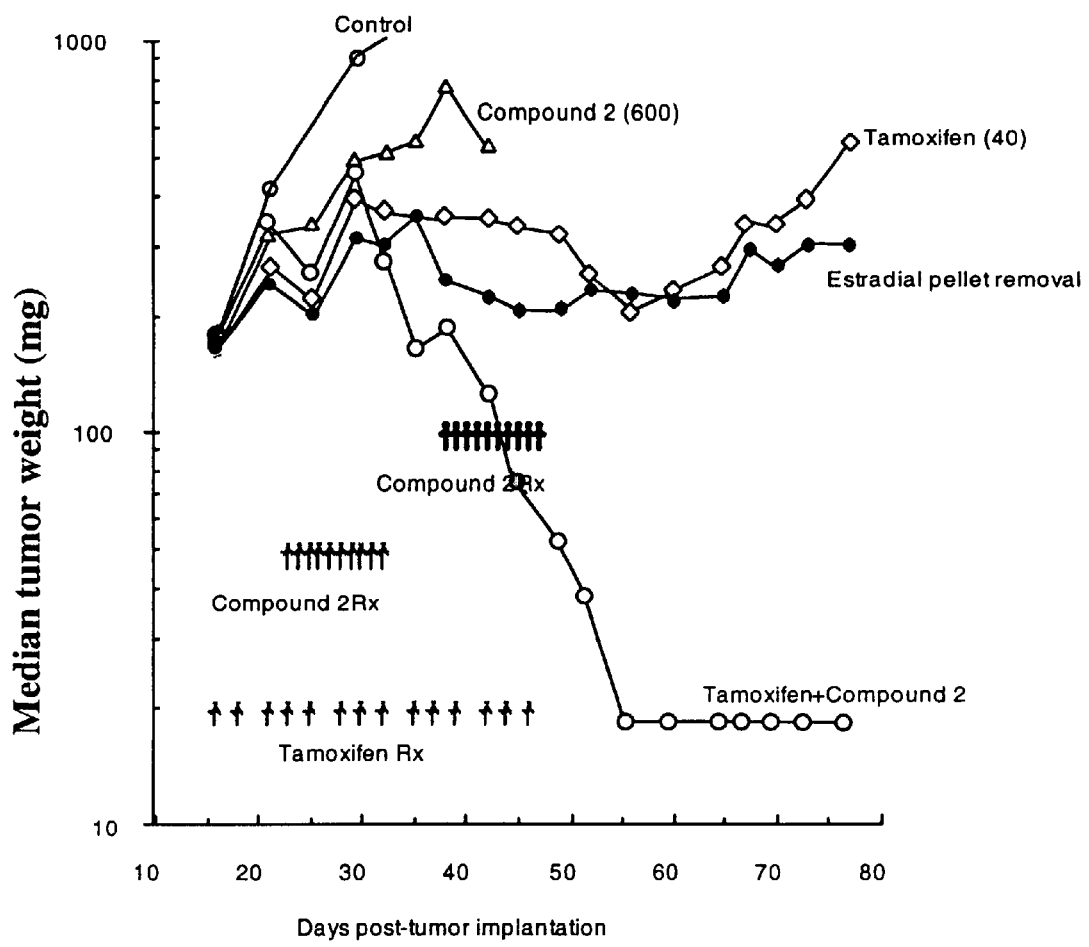
FIG. 20 Compound 2 enhances the antitumor activity of Tamoxifen in the MCF-7 estrogen-dependent human breast carcinoma xenograft model in nude mice. Tamoxifen was administered PO, Q2D×14. Compound 2 was administered PO for 2 courses, Q1D×10, as illustrated in the figure.

Tamoxifen in Combination with the Compounds of the Invention Acts Synergistically to Kill Cancer Cells in an Oestrogen-dependent Human Breast Cancer Xenograft The majority of human breast cancers require estrogen for growth and tumor progression (estrogen-dependent). Treatment of estrogen-dependent breast cancers with antiestrogens, such as tamoxifen, has been shown to inhibit tumor cell proliferation both in vitro and in vivo. In order to assess the efficacy of the combined anti-cancer agents of the invention in a human breast cancer model, MCF-7 xenografts were grown in nude mice and treated as described herein. Combination chemotherapy using Compound 2 and tamoxifen resulted in enhanced antitumor activity. Indeed, tumor remission was observed in 3 of 8 mice in the MCF-7 human breast cancer xenograft model. FIG. 20 shows that Compound 2 administered as a single agent produced only a very modest effect on tumor growth. Tamoxifen alone was markedly more active in this model, roughly as effective as estradial pellet removal, but nonetheless after treatment with tamoxifen, or pellet removal, all tumors regrew and no cures were observed. By contrast, 40 mpk of tamoxifen in combination with Compound 2 (po, 100 mpk, qd×10, two courses) resulted in a dramatic decrease in median tumor weight, in addition to the above-mentioned cures.

EXAMPLE 11

Androgen-ablation Therapy (Surgical or Chemical) Enhances the Sensitivity of Androgen-dependent Human Prostate Cancer to Compound 2 by Inducing a Non-proliferative State in Tumor Cells (Quiescence)

As mentioned previously, cells are rendered non-proliferative or "quiescent" under a variety of biological conditions. One conventional approach to the treatment of human prostate cancer is chemical castration. While the invention is not dependent on any particular theory or mechanism, it is believed that in an androgen-dependent prostate cancer, hormone ablation acts as a pro-quiescence agent by removing the growth stimuli critical to the tumor proliferation. The efficacy of the anti-cancer agents of the invention was therefore assessed in a human prostate cancer xenograft model.

Figure 21:
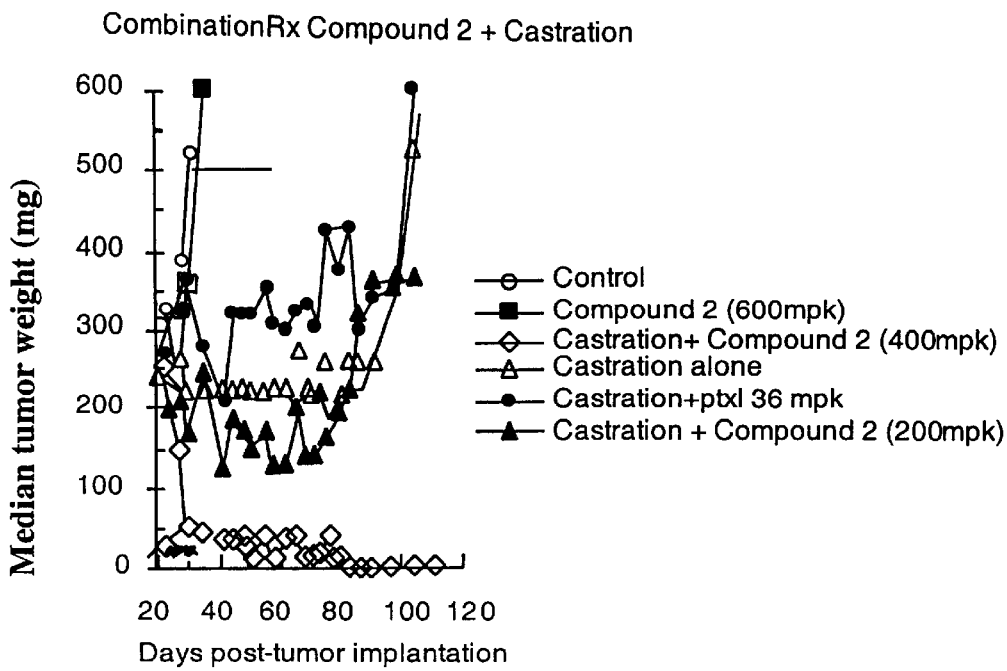
FIG. 21 Compound 2 enhances the antitumor activity of surgical castration in an androgen-dependent human prostate carcinoma xenograft model MDA-PCa-2b in nude mice. Surgical castration was performed on Day 21 post-tumor implantation. Compound 2 and paclitaxel therapy was initiated 3 days following surgical castration. Compound 2 was administered PO, Q1D×10. Paclitaxel was given IV, Q2D×5.

In the androgen-dependent sc MDA-Pca-2b human prostate carcinoma xenograft model, treatment with Compound 2 alone (400 mpk, po, q1d×10) had a modest effect on tumor growth, as shown in FIG. 21. Androgen ablation therapy (surgical castration) also reduced the rate of tumor growth, but did not cause regression. As the data reveal (FIG. 21 administration of Compound 2 three days after castration resulted in rapid tumor regression.

Figure 22:
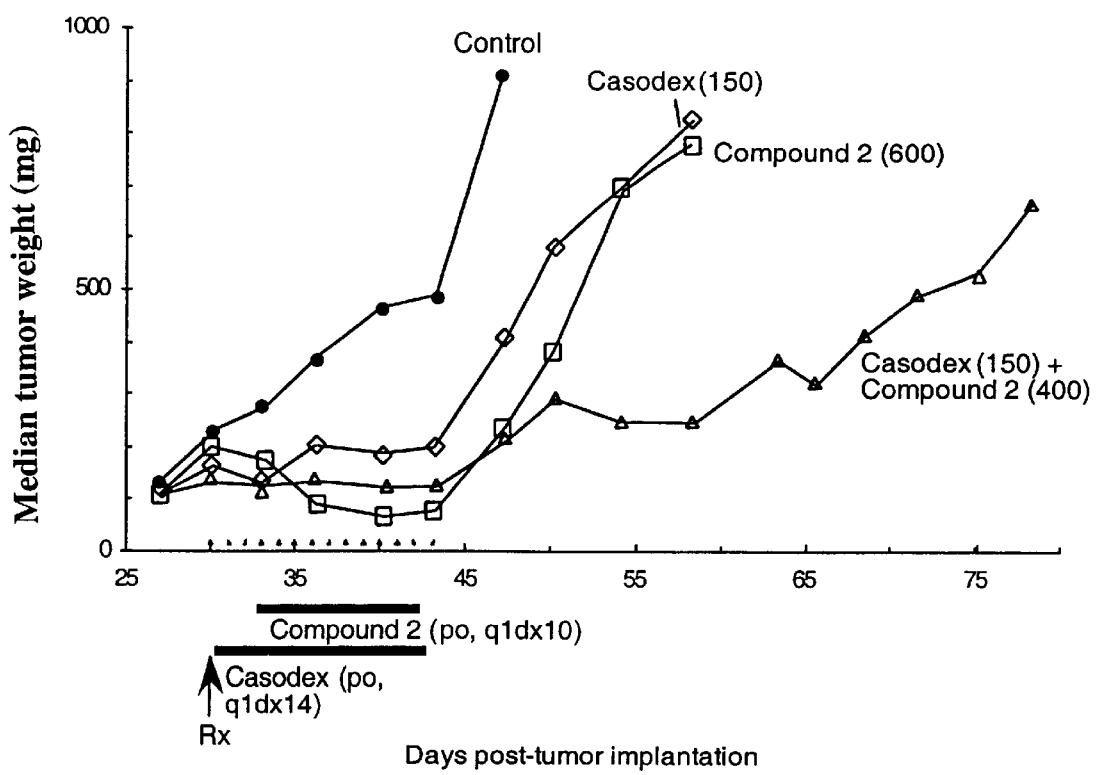
FIG. 22 Compound 2 enhances the antitumor activity of the androgen receptor inhibitor Casodex® against an androgen-independent, Casodex®-responsive human prostate carcinoma xenograft model MDA-PCa-2b-AI in nude mice. Casodex® was administered PO, Q1D×10. Compound 2 therapy was initiated 3 days following Casodex®. Compound 2 was administered PO, Q1D×10.

Another method of rendering androgen-dependent prostate carcinoma cells non-proliferative is the use of chemical anti-androgen agents, such as Casodex®. Indeed, it is now known that some prostate carcinomas remain sensitive to Casodex® therapy even after they become increasingly androgen-independent, and vice versa. This phenomenon has been hypothesized to result from specific mutations in the androgen receptor which differentially affect androgen and anti-androgen receptor binding. To test the antitumor efficacy of combining Casodex® and Compound 2, we employed the Casodex®-responsive but androgen-independent human prostate ca. model Pca-2b-AI. As shown in FIG. 22, the combined effects of Casodex® and Compound 2 were significantly greater in this tumor model than the effects of either of the agents used alone, both being administered at their maximum tolerated doses and regimens (600 mpk, po, q1D×10 for Compound 2; 150 mpk, po, q1D×4 for Casodex®, respectively). Thus, by definition, the combination of Casodex® and Compound 2 produced synergistic antitumor activity that surpassed each of the agents given singly.

EXAMPLE 12

Compound 2 in Combination with a cdk Inhibitor (Compound 9) Produced Synergistic Cell Killing Effects in a Strictly Sequence Dependent Manner (FIG. 23)

Mitotic division of mammalian cells requires the coordinated activities of a family of serine/threonine protein kinases, known as the cyclin-dependent kinases (CDKs). Inhibitors of CDKs, specifically CDK2, have been shown to inhibit cell proliferation and arrest cells in the G1/S boundary of the cell cycle. To determine the effects of combination chemotherapy with CDKs inhibitor (CDKI) and Compounds of the present invention, a study was conducted whereby exponentially proliferating A2780s human ovarian carcinoma cells were treated for a 4 hour period with 1.5 μM of a selective CDK2 inhibitor. Compound 9 (no effect dose) was combined with a 20 hour treatment of increasing concentrations of Compound 2. Two treatment sequences were employed: (1) Compound 9 for 4 hours followed by Compound 2 for 20 hours, or (2) Compound 2 for 20 hours followed by Compound 9 for 4 hours. As shown in FIG. 23, synergistic cell killing was observed when the CDKI was administered first, while no effects were observed when Compound 2 was given first. This supports the hypothesis that by administering the CDKI first, cells were rendered non-proliferative which in turn sensitized them to the cytotoxic action of Compound 2.

EXAMPLE 13

Conversion of Epothilone B to Epothilone F

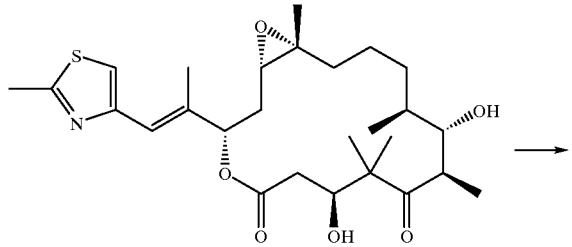

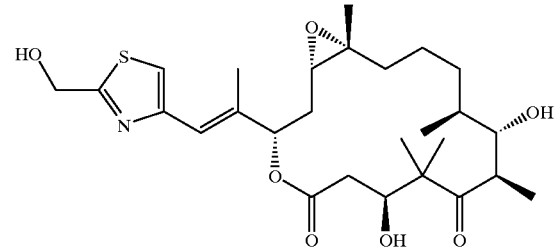

(i) 1.98 g (3.90 mmol) of Epothilone B was placed under Argon and dissolved in 60 mL dry $CH_2Cl_2$. To this solution was added 0.720 g mCPBA (4.17 mmol, 1.07 equivalents). The mixture was allowed to stir at 25° C. for 5.5 hours. The reaction mixture was quenched with 60 mL $NaHCO_3$, and extracted with 3×75 mL of $CHCl_3$. The organic phase was washed with 100 mL water followed by 70 mL of 5% $Na_2SO_3$(aq) and then 70 mL brine. The organic phase was then dried over $Na_2SO_4$. The crude reaction product was chromatographed using silica gel eluting with 2% MeOH in $CHCl_3$ to yield 0.976 g of the N-oxide (48%) as a white fluffy solid.

(ii) To a resealable tube under Argon was added 0.976 g of the N-oxide (1.86 mmol) dissolved in 35 mL dry $CH_2Cl_2$, 2,6-lutidine (1.73 mL, 14.88 mmol, 8 equivalents) and $(CF_3CO)_2O$ (1.84 mL, 13.02 mmol, 7 equivalents). The tube was sealed and heated at 70° C. for 25 min. The mixture was allowed to cool and the solvent was removed under a stream of argon, followed by concentration to a few mL of dark yellow solution under vacuum. The reaction was diluted with 25 mL MeOH and 2.9 mL of 28% $NH_4OH$ (aq) was added. The mixture was heated to 45° C. for 20 min, then cooled to room temperature. The crude product was concentrated on the rotary evaporator and chromatographed using silica gel eluting with 4% MeOH in $CHCl_3$ to yield 0.815 g of Epothilone F (84%).

EXAMPLE 14

Preparation of [1S-[1R*,3R*(E),7R*,10S*,11R*, 12R*,16S*]]-3-[2-[2-(Azidomethyl)-4-thiazolyl]-1-methylethenyl]-7,11-dihydroxy-8,8,10,12,16-pentamethyl-4,17-dioxabicyclo[14.1.0]heptadecane-5,9-dione

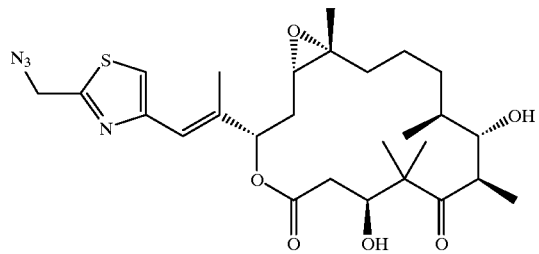

To a stirred solution of epothilone F from Example 13 above (957 mg, 1.83 mmol) in 20.0 mL tetrahydrofuran at 0° C. under Argon was added 0.47 mL diphenylphosphoryl azide (604 mg, 2.19 mmol, 1.2 equivalents). The mixture was stirred for approximately 3 min. 1,8-diazabicyclo[5.4.0] undec-7-ene (0.27 mL, 278 mg, 1.83 mmol, 1 equivalent) was then added and the mixture was stirred at 0° C. After 2 hours, the mixture was warmed to 25° C. and stirred for 20 hours. The reaction mixture was diluted with 150 mL ethyl acetate and washed with 50 mL H$_2$O. The aqueous layer was extracted with 35 mL ethyl acetate. The combined organic layers were dried over Na$_2$SO$_4$ and concentrated under vacuum. The crude material was chromatographed using silica gel eluted with 50% ethyl acetate in hexanes to afford 913 mg (91%) of 21-azido-epothilone B, as a clear, colorless oil. MS (ESI$^+$): 549.3 (M+H)$^+$; $^1$H-NMR (300 MHz, CDCl$_3$); δ=6.59 (bs, 17-H), 7.04 (s, 19-H), 4.63 (s, 21-H$_2$); HRMS (DCI); C$_{27}$H$_{40}$N$_4$O$_6$S: [M$^+$] calculated 549.2747, found 549.2768.

EXAMPLE 15

Preparation of [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione Lindlar catalyst, 18.0 mg, was suspended in 500 µL of ethanol in an H$_2$ atmosphere and was saturated. Then, 15.9 mg (29.0 µmol) of 21-azido-epothilone B from Example 14 above, dissolved in an ethanol-methanol mixture, was added. After stirring for 30 minutes at room temperature, the suspension was filtered through diatomaceous earth, and washed with ethyl acetate. The solvent was removed from the organic phase and dried in high vacuum. The purification of the crude product was done through PSC (solvent: CH$_2$Cl$_2$/methanol 90:10), whereupon 12.3 mg (81%) of 21-amino-epothilone B and 1 mg (6%) of educt is obtained.

$^1$H-NMR (300 MHz, CDCl$_3$); δ=6.58 (bs, 17-H), 7.05 (s, 19-H), 4.15 (s, 21-H$_2$); HRMS (DCI); C$_{27}$H$_{42}$N$_2$O$_6$S: [M+H$^+$] calculated 522.2764, found 522.2772.

EXAMPLE 16

Preparation of [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione (Alternative Method)

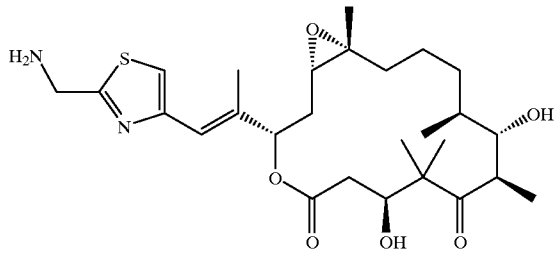

To a stirred solution of 21-azido-epothilone B (Example 14) (1.070 g, 1.950 mmol) in 30.0 mL tetrahydrofuran under Argon was added 0.22 mL of trimethylphosphine (0.163 g, 2.145 mmol, 1.1 equivalents). H$_2$O (5.5 mL) was then added, and the mixture was allowed to stir at 25° C. After 3 hours, the azide was completely consumed and 3 mL of 28% aqueous NH$_4$OH was added to complete the conversion of phosphoryl imine to amine. After stirring at 25° C. for 1 hour the solvents were removed under vacuum. The crude material was chromatographed using silica gel eluted with 1% Et$_3$N, 2.5% MeOH in CHCl$_3$ to yield 924 mg (91%) of 21-amino-epothilone B, as a white solid. MS (ESI$^+$): 523.3 (M+H)$^+$.

EXAMPLE 17

Preparation of (+)-cis-4-tert-Butyl-1-tert-butyloxycarbonyl-3-triethylsilyloxy-azetidin-2-one

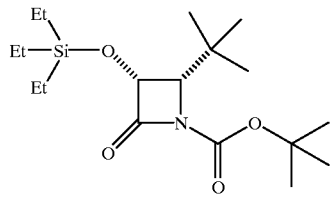

Trimethylacetaldehyde (20.3 mL, 1.25 equiv) was added to a stirred suspension of p-anisidine (18.4 gm, 0.150 mole) and anhydrous Na$_2$SO$_4$ (150 gm) in anhydrous dichloromethane (250 mL) at room temperature. After 2 hr, this was filtered and the solid was washed with additional anhydrous dichloromethane. The solvent was removed from the filtrate and the crystalline residue was dissolved in anhydrous dichloromethane (750 mL) and placed under a nitrogen atmosphere. Triethylamine (48.0 mL, 2.3 equiv) was added and the reaction was cooled to −78° C. Benzyloxyacetyl chloride (27.2 mL, 1.15 equiv) was added dropwise and then the reaction was allowed to warm to room temperature. After 24 hr, this was washed with 0.5 M HCl (twice), sat. aqueous NaHCO$_3$ solution, brine and dried (Na$_2$SO$_4$). The solvent was removed and the residue was chromatographed on a silica gel column (gradient elution with 20% dichloromethane in hexane containing 0 to 20% EtOAc) to afford (+)-cis-4-tert-butyl-3-benzyloxy-1-p-methoxybenzyl-azetidinone as a crystalline solid (46.9 gm, 92%): $^1$H NMR (CDCl$_3$) δ 1.09 (s, 9H), 3.81 (s, 3H), 4.15 (d, 1H, J=5.5 Hz), 4.77 (d, 1H, J=11.9 Hz), 4.81 (d, 1H, J=5.5 Hz), 5.03 (d, 1H, J=11.9 Hz), 6.87–7.43 (m, 9 Hz); LRMS (ESI) 340 ([M+H]$^+$). A solution of ceric ammonium nitrate (60.4 gm, 3.6 equiv) in 900 mL of water was added to a well stirred solution of the azetidinone (10.38 gm, 30.6 mmole) in acetonitrile (600 mL) in an ice bath over 1 hr. The reaction was then extracted with EtOAc (twice) and the combined organic extracts were washed with sat. aqueous NaHCO$_3$ solution (twice), 20% aqueous NaHSO$_3$ solution, sat. aqueous NaHCO$_3$ solution and brine. After being dried (Na$_2$SO$_4$), the solvents were removed and the residue was chromatographed on a silica gel column (gradient elution with portions of hexane containing 10 to 40% EtOAc) to afford 5.64 gm of slightly impure (+)-cis-3-benzyloxy-4-tert-butyl-azetidin-2-one: $^1$H NMR (CDCl$_3$) δ 1.04 (s, 9H), 3.51 (d, 1H, J=5.2 Hz), 4.71 (m, 2H), 4.96 (d, 1H, J=11.9 Hz), 6.10 (brs, 1H), 7.35 (m, 5H). A suspension of this material (5.54 gm, 23.8 mmole) and 2.5 gm of 10% Pd on charcoal in absolute EtOH (100 mL) was hydrogenated (34 psi H$_2$, Parr apparatus) for 23 hr. A further 2 gm of the Pd catalyst was added and the hydrogenation was continued for a further 17 hr at 50 psi H$_2$. The catalyst was removed by filtration and the solvent was removed from the filtrate to leave crude (+)-cis-3-hydroxy-4-(tert-butyl)-azetidin-2-one: $^1$H NMR (CDCl$_3$+1 drop D$_2$O) δ 1.05 (s, 9H), 3.48 (d, 1H, J=5.0 Hz), 4.98 (d, 1H, J=5.0 Hz). This material was dissolved in dry N,N-dimethylformamide (40 mL) and imi dazole (3.24 gm, 2 equiv) and triethylsilyl chloride (4.0 mL, 1 equiv) were added. After 10 min, the reaction was partitioned between water and a mixture of EtOAc and hexane (1:1). The organic phase was washed with water (twice), brine and then dried ($Na_2SO_4$). The solvents were removed and the residue was chromatographed on a silica gel column (gradient elution with 20 to 25% EtOAc in hexane) to give (+)-cis-4-tert-butyl-3-triethylsilyloxy-azetidin-2-one (3.86 gm): $^1$H NMR ($CDCl_3$) δ 0.70 (m, 6H), 0.98 (m, 18H), 3.39 (d, 1H, J=5.0 Hz), 4.88 (dd, 1H, J=2.1, 5.0 Hz), 6.08 (brs, 1H). A solution of this azetidinone (2.04 gm, 7.92 mmole), diisopropylethyl amine (1.66 mL, 1.2 equiv), di-tert-butyl dicarbonate (1.90 gm, 1.1 equiv) and p-dimethylaminopyridine (194 mg, 0.2 equiv) in dry dichloromethane (24 mL) was stirred at room temperature for 3 hr. The reaction mixture was diluted with dichloromethane, washed with brine and dried ($Na_2SO_4$). Removal of the solvent followed by silica gel column chromatography (gradient elution with 0 to 20% EtOAc in hexane) afforded 2.71 gm (96%) of the title compound as an oil: $^1$H NMR ($CDCl_3$) δ 0.70 (m, 6H), 1.00 (m, 9H), 1.09 (s, 9H), 1.53 (s, 9H), 3.90 (d, 1H, J=6.5 Hz), 4.93 (d, 1H, J=6.5 Hz).

EXAMPLE 18

Preparation of Baccatin Derivative A

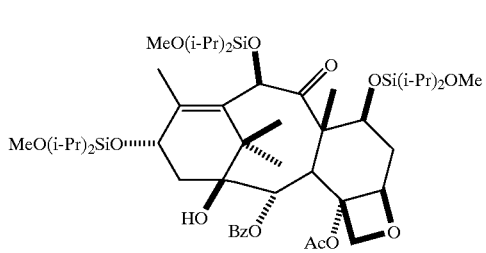

(A)

To a solution of 10-desacetylbaccatin (47.4 g, 87 mmol) in anhydrous N,N-dimethylformamide (DMF) (500 mL) was added imidazole (47 g, 691 mmol) at ambient temperature. Solution was stirred for 10–15 min until a clear solution was observed. Dropwise, diisopropyldichlorosilane (58 mL, 322 mmol) was added to the reaction mixture. Reaction mixture was stirred for 16 h at ambient temperature. Additional amount of diisopropyldichlorosilane (6 mL) was added to the solution and the reaction mixture was stirred for 60 min. HPLC at this point indicated completion of the reaction. Methanol (36 mL) was added to the mixture and the solution was stirred for 60 min. Reaction was stopped and diluted with a mixture of tert-butyl methyl ketone (TBME) (500 mL) and water (200 mL). Layers were separated and organic phase was washed with brine (250 mL), dried (sodium sulfate) and evaporated to afford the trisilylated baccatin derivative A, (91 g, >100% yield) as a white amorphous compound which was used in the next step without further purification.

LRMS(ESI)M+ calcd. For $C_{50}H_{84}O_{13}Si_3$: 977. Found 977.

EXAMPLE 19

Preparation of Baccatin Derivative B

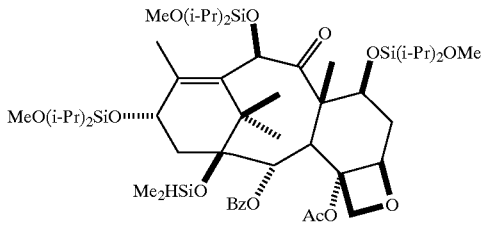

(B) To a solution of baccatin derivative A (90 g, 92 mmol) in DMF (500 mL) was added imidazole (22 g, 320 mmol) at 0° C. Dimethylchlorosilane (35 mL, 320 mmol) as added dropwise at 0° C. Precipitation of the compound was observed at this point. Reaction mixture (slurry) was stirred for 0.5 h at 0° C. Solid was filtered and washed with cold DMF (3×150 mL). After air drying, solid was redissolved in TBME (700 mL) and the solution was washed with water (3×200 mL), brine (250 mL) and dried (sodium sulfate). The solution was filtered through a short silica pad. Removal of the solvent under vacuum afforded B in 77% yield (70 g).

LRMS(ESI)M+ calcd. For $C_{50}H_{90}O_3Si_4$: 1035. Found 1035.

EXAMPLE 20

Preparation of Baccatin Derivative C

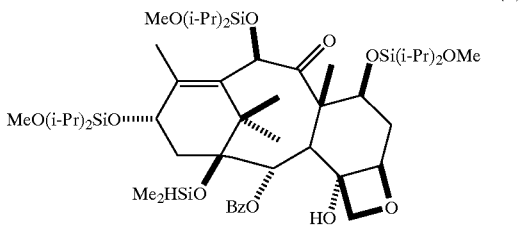

(C)

To a stirred solution of B (66.3 g, 64 mmol) in toluene (680 mL) at −34° C. was added Red-Al® (50 mL, 160 mmol, 65 wt % solution of sodium bis(2-methoxyethoxy)aluminum hydride in toluene) dropwise over a period of 10 min. Reaction mixture was warmed to −25° C. and stirred for 1.5 h. Methanol (62 mL) was added dropwise to the reaction mixture keeping internal temperature between −20 and −25° C. Solution was diluted with TBME (500 mL) followed by the addition of 1 N sodium hydroxide solution (60 mL) and brine (60 mL). Solution was stirred for 30 min. Diatomaceous earth (12 g) was added to the mixture, stirred for 10 min, and filtered through a pad of diatomaceous earth. Layers were separated. Organic layer was washed with water, brine, and dried (sodium sulfate). Next, solution was passed through a short silica pad before removal of the solvent. The compound was obtained in 97% yield (62 g) as a white solid.

LRMS(ESI)M+ calcd. For $C_{50}H_{88}O_{12}Si_4$: 993. Found 993.

EXAMPLE 21

Preparation of Baccatin Derivative D

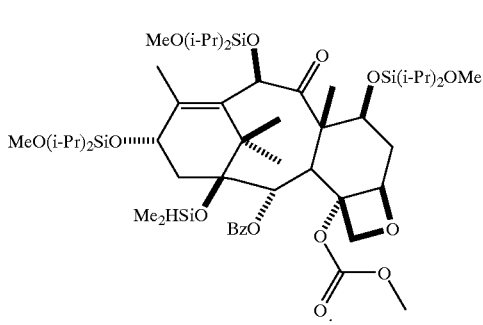

Under argon atmosphere, to a solution of baccatin derivative C (62 g, 62 mmol) in anhydrous tetrahydrofuran (THF) (600 mL) at −60° C. was added lithium bis(trimethylsilyl)amide (125 mL, 125 mmol, 1 M solution in THF) dropwise. Solution was stirred for 15 min followed by the addition of methyl chloroformate (9 mL, 116 mmol); internal temperature of the solution was maintained at −60° C. Reaction was slowly warmed to 0° C. and mixture was stirred for 3 h. After completion of the reaction, saturated ammonium chloride (300 mL) was added. Reaction mixture was extracted with TBME (100 mL). Organic layer was washed with saturated ammonium chloride (200 mL), water (200 mL), brine (200 mL), dried (sodium sulfate), and evaporated to provide D as an oil (67 g, >100%). The crude material was used in the next step without further purification.

LRMS(ESI)M+ calcd. For $C_{52}H_{90}O_{14}Si_4$: 1051. Found 1051.

EXAMPLE 22

Preparation of Baccatin Derivative E

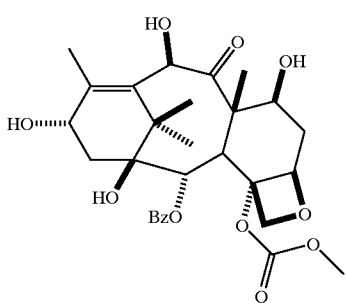

To a solution of baccatin derivative D (62 g, 59 mmol) in dry THF (260 mL) was added triethylamine-hydrofluoric acid complex (56 mL, 344 mmol) at ambient temperature. Reaction was stirred for 3 h. Reaction mixture was diluted with ethyl acetate (350 mL) and washed with water (200 mL), brine (200 mL), dried (sodium sulfate), and evaporated to afford E (43 g, >100% crude yield). Reslurring of the crude compound in a mixture of hot ethyl acetate (350 mL) and hexanes (50 mL) gave pure E in 90% yield.

LRMS(ESI)M+ calcd. For $C_{29}H_{36}O_{11}$: 560. Found 560.

EXAMPLE 23

Preparation of Baccatin Derivative F

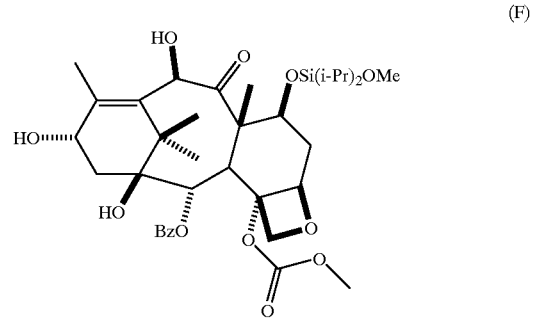

To a stirred solution of baccatin derivative E (32 g, 57 mmol) and imidazole (11.7 g, 172 mmol in DMF (220 mL)) at −65° C. was added diisopropyldichlorosilane (26.8 mL) under argon. Temperature of the reaction mixture was maintained at −60° C. and the mixture was stirred for 2 h. After completion of the reaction (HPLC), a solution of imidazole in methanol (11.7 g imidazole dissolved in 35 mL methanol) was added and the solution was stirred at 0° C. for 30 min. Mixture was extracted with TBME (500 mL). Organic phase was washed with water (4×150 mL), dried (sodium sulfate), and evaporated to afford crude F (45 g). The crude material was further dissolved in acetonitrile (150 mL) and the solution was washed with hexanes (3×100 mL). Removal of acetonitrile afforded pure F as a white solid (34 g, 84% yield).

LRMS(ESI)M+ calcd. For $C_{36}H_{52}O_{12}Si$: 704. Found 704.

EXAMPLE 24

Preparation of 4-deacetyl-7-[bisisopropyl(methoxy)]silyloxy-4-methoxycarbonyl-baccatin

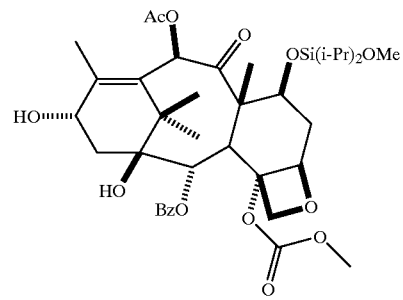

To a solution of baccatin derivative F (33.2 g, 47 mmol) in DMF (200 mL) was added lithium bis(trimethylsilyl)amide (61.2 mL, 61.2 mmol, 1 M solution in THF) dropwise at −43° C. The reaction mixture was stirred for 15 min followed by the addition of acetic anhydride (5.8 mL, 63 mmol). The reaction mixture was stirred for 30 min. at −40° C. Acetic acid (3.6 mL) was added and the cooling bath was removed. The reaction mixture was extracted with TBME (300 mL). Organic layer was separated and washed with water (3×150 mL), brine (150 mL), dried (sodium sulfate), and evaporated to afford the crude product. Purification of this compound was achieved by crystallization from a mixture of THF:heptane (1:6). Input of 40 g provided 21 g of crystallized title product (60% yield).

LRMS(ESI)M+ calcd. For $C_{38}H_{54}O_{13}Si$: 746. Found 746.

EXAMPLE 25

Preparation of 3'-tert-Butyl-3'-N-tert-butyloxycarbonyl-4-deacetyl-3'-dephenyl-3'-N-debenzoyl-4-O-methoxycarbonyl-paclitaxel

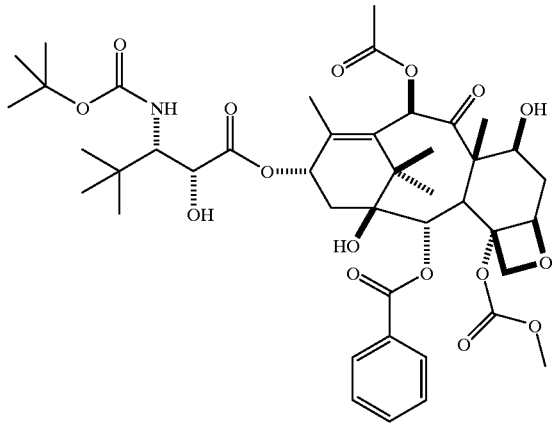

A solution of (+)-cis-4-tert-butyl-1-(tert-butyloxycarbonyl)-3-triethylsilyloxy-azetidin-2-one (2.71 gm, 5 equiv) and 4-deacetyl-7-[bisisopropyl(methoxy)]silyloxy-4-methoxycarbonyl-baccatin (1.13 gm, 1.52 mmole) in dry THF (100 mL) under $N_2$ was cooled to $-50°$ C. and a solution of lithium bis(trimethylsilyl)amide (1.97 mL, 1.3 equiv, 1.0 M in THF) was added. After 5 min this was transferred to a bath that was maintained at $-35$ to $-30°$ C. for 20 hr and then $-25°$ C. for 24 hr. The reaction was then quenched with saturated aqueous $NH_4Cl$ solution and extracted with a mixture of EtOAc and hexane (1:1). The organic extracts were washed with brine and dried ($Na_2SO_4$). The solvents were removed and the residue was chromatographed (radial chromatography on a 6 mm silica gel plate; gradient elution with 5 to 20% EtOAc in hexane) to afford 1.55 gm of 3'-tert-butyl-3'-N-tert-butyloxycarbonyl-7-[bisisopropyl(methoxy)]silyloxy-4-deacetyl-3'-dephenyl-3'-N-debenzoyl-4-O-methoxycarbonyl-2'-triethylsilyloxy paclitaxel as a mixture of 2',3'-diastereomers. This mixture was dissolved in dry THF (60 mL) and triethylamine trihydrofluoride (0.92 mL 4 equiv) was added. After 22 hr at room temperature, the reaction mixture was neutralized with saturated aq. $NaHCO_3$ solution and then extracted with EtOAc. The organic extracts were washed with brine, dried ($Na_2SO_4$) and the solvents were removed. The residue was chromatographed (radial chromatography; 2 mm silica gel plate; gradient elution from 10 to 50% EtOAc in hexane) to afford (in order of elution): 210 mg (18%) of 2'S,3'R-3'-tert-butyl-3-'N-tert-butyloxycarbonyl-4-deacetyl-3'-dephenyl-3'-N-debenzoyl-4-O-methoxycarbonyl-paclitaxel {$^1$H NMR (CDCl$_3$) δ 1.04 (s, 9H), 1.13 (s, 3H), 1.20 (s, 3H), 1.37 (s, 9H), 1.65 (s, 1H), 1.66 (s, 3H), 1.84–1.93 (m, 2H), 2.17 (s, 3H), 2.25 (s, 3H), 2,55 (m, 3H), 3.00 (d, 1H, J=6.5 Hz), 3.74 (d, 1H, J=10.8 Hz), 3.79 (d, 1H, J=6.9 Hz), 3.92 (s, 3H), 4.16 (d, 1H, J=8.5 Hz), 4.33 (d, 1H, J=8.5 Hz), 4.42 (m, 1H), 4.54 (d, 1H, J=6.5 Hz) 4.87 (d, 1H, J=10.6 Hz), 5.01 (d, 1H, J=7.7 Hz), 5.68 (d, 1H, J=7.0 Hz), 5.76 (m, 1H), 6.32 (s, 1H), 7.44–8.05 (m, 5H); LRMS (ESI) 846 [(M+H)$^+$]} and 668 mg (56%) of the title compound {$^1$H NMR (CDCl$_3$) δ 1.07 (s, 9H), 1.14 (s, 3H), 1.24 (s, 3H), 1.33 (s, 9H), 1.66 (s, 4H), 2.23 (s, 3H), 2.38–2.59 (m, 4H), 3.11 (d, 1H, J=5.8 Hz), 3.77 (d, 1H, J=11.1 Hz), 3.82 (d, 1H, J=7.0 Hz), 3.96 (s, 3H), 4.20 (d, 1H, J=8.6 Hz), 4.33 (d, 1H, J=8.6 Hz), 4.39 (m, 1H), 4.53 (d, 1H, J=5.4 Hz) 4.88 (d, 1H, J=10.6 Hz), 4.98 (d, 1H, J=7.9 Hz), 5.69 (d, 1H, J=7.1 Hz), 6.03 (m, 1H), 6.28 (s, 1H), 7.40–8.11 (m, 5H); LRMS (ESI) 846 [(M+H)$^+$]}.

The present invention is not limited to the embodiments specifically described above, but is capable of variation and modification without departure from the scope of the appended claims.

What is claimed is:

1. A method for the treatment of cancer which comprises administering to a mammalian specie in need thereof a synergistically, therapeutically effective amount of (1) at least one agent selected from the group consisting of antiproliferative cytotoxic agents and cytostatic agents and (2) a compound of formula I

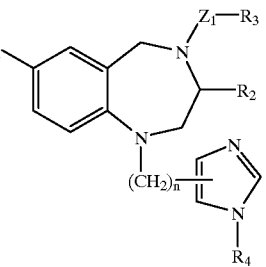

(I)

or a pharmaceutically acceptable salt thereof wherein $R_1$ is Cl, Br, CN, optionally substituted phenyl, or optionally substituted 2-,3- or 4-pyridyl;

$R_2$ is optionally substituted lower alkyl, or optionally substituted aralkyl;

$R_3$ and $R_5$ are each independently optionally substituted lower alkyl, optionally substituted aryl, or optionally substituted heterocyclo;

$R_4$ is hydrogen or lower alkyl;

$Z_1$ is CO, $SO_2$, $CO_2$ or $SO_2N(R_5)$—; and n is 1 or 2;

provided that the cytotoxic agent and/or cytostatic agent is administered simultaneously with or prior to the formula I compound.

2. The method according to claim 1 wherein the cytotoxic agent is administered prior to the formula I compound.

3. The method according to claim 1 wherein the cytotoxic agent comprises radiation therapy.

4. The method according to claim 1, wherein the cytostatic agent is administered prior to the formula I compound.

5. The method according to claim 1 for the synergistic treatment of cancerous solid tumors.

6. The method according to claim 1 wherein the cytotoxic agent is selected from the group consisting of a microtubule-stabilizing agent, a microtubule-disruptor agent, an alkylating agent, an anti-metabolite, epidophyllotoxin, an antineoplastic enzyme, a topoisomerase inhibitor, procarbazine, mitoxantrone, and a platinum coordination complex.

7. The method according to claim 1 wherein the cytotoxic agent is selected from the group consisting of an anthracycline drug, a vinca drug, a mitomycin, a bleomycin, a cytotoxic nucleoside, a taxane, an epothilone, discodermolide, a pteridine drug, a diynene, an aromatase inhibitor and a podophyllotoxin.

8. The method according to claim 1 wherein the cytotoxic agent is selected from the group consisting of paclitaxel, docetaxel, 7-O-methylthiomethyl-paclitaxel, 4-desacetyl-4-methylcarbonatepaclitaxel, 3'-tert-butyl-3'-N-tertbutyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, vindesine, leurosine, estramustine, cisplatin, carboplatin, cyclophosphamide, bleomycin, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, a pyridobenzoindole, an interferon and an interleukin.

9. The method according to claim 1 wherein the cytotoxic agent is selected from the group consisting of a taxane and an epothilone.

10. The method according to claim 1 wherein the cytotoxic agent is selected from the group consisting of paclitaxel, docetaxel, 7-O-methylthiomethyl-paclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]4-aza-17-oxabicyclo[14.1.0]heptadecane-5,9-dione and [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

11. The method according to claim 1 wherein
$R_1$ is Br, or CN;
$R_2$ is optionally substituted benzyl;
$R_3$ is optionally substituted lower alkyl, optionally substituted phenyl, optionally substituted 2-thienyl, or optionally substituted 1-piperidinyl;
$R_4$ is hydrogen, or methyl;
$Z_1$ is CO, $SO_2$, or $SO_2N(R_5)$—;
$R_5$ is optionally substituted lower alkyl or optionally substituted phenyl; and n is 1.

12. The method according to claim 1 wherein
$R_1$ is CN;
$R_2$ is optionally substituted benzyl;
$R_3$ is optionally substituted lower alkyl, optionally substituted phenyl, optionally substituted 2-thienyl, or optionally substituted 1-piperidinyl;
$R_4$ is hydrogen, or methyl;
Z is CO, or $SO_2$; and
n is 1.

13. The method according to claim 1 wherein
$R_1$ is CN;
$R_2$ is benzyl;
$R_3$ is n-propyl, n-butyl, 3-methoxypropyl, 2-thienyl, 5-bromo-2-thienyl, phenyl, 4-methoxyphenyl, or 1-piperidinyl;

$R_4$ is hydrogen;
Z is $SO_2$; and
n is 1.

14. The method according to claim 1 wherein the formula I compound is selected from the group consisting of
(R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile;
(R)-7-cyano-2,3,4,5-tetrahydro-1-(1H-imidazol-4-ylmethyl)-4-(1-oxobutyl)-3-(phenylmethyl)-1H-1,4-benzodiazepine;
(R)-4-[(5-bromo-2-thienyl)sulfonyl]-7-cyano-2,3,4,5-tetrahydro-1-(1H-imidazol-4-yl methyl)-3-(phenyl methyl)-1H-1,4-benzodiazepine;
(R)-7-cyano-2,3,4,5-tetrahydro-1-(1H-imidazol-4-yl methyl)-4-[(4-methoxyphenyl)sulfonyl]-3-(phenylmethyl)-1H-1,4-benzodiazepine;
(R)-7-cyano-2,3,4,5-tetrahydro-1-(1H-imidazol-4-ylmethyl)-3-(phenyl methyl)-4-(phenylsulfonyl)-1H-1,4-benzodiazepine;
(R)-7-cyano-2,3,4,5-tetrahydro-1-(1H-imidazol-4-ylmethyl)-3-(phenylmethyl)-4-(propylsulfonyl)-1H-1,4-benzodiazepine;
(R)-4-(butylsulfonyl)-7-cyano-2,3,4,5-tetrahydro-1-(1H-imidazol-4-ylmethyl)-3-(phenylmethyl)-1H-1,4-benzodiazepine;
(R)-7-cyano-2,3,4,5-tetrahydro-1-(1H-imidazol-4-ylmethyl)-3-(phenylmethyl)-4-(1-piperidinylsulfonyl)-1H-1,4-benzodiazepine;
(R)-4-(3-methoxypropylsulfonyl)-7-cyano-2,3,4,5-tetrahydro-1-(1H-imidazol-4-ylmethyl)-3-(phenylmethyl)-1H-1,4-benzodiazepine; and
pharmaceutically acceptable salts thereof.

15. The method according to claim 14 wherein the pharmaceutically acceptable salt is selected from the group consisting of the hydrochloride salt, the methanesulfonic acid salt and the trifluoroacetic acid salt.

16. The method according to claim 10 wherein the formula I compound is (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

17. The method according to claim 1 wherein the cytotoxic agent is paclitaxel and the formula I compound is (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

18. The method according to claim 1 wherein the cytotoxic agent is [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione and the formula I compound is
(R)-2,3,4,5-tetrahydro-1-(1H-imidazol-4-yl methyl)-3-(phenylmethyl)-4-(2-thienylsulfonyl)-1 H-1,4-benzodiazepine-7-carbonitrile or a pharmaceutically acceptable salt thereof.

19. The method according to claim 1 wherein the mammalian specie is a human.

20. The method according to claim 1 wherein the cytostatic agent is selected from the group consisting of surgical castration, chemical castration, tamoxifen, 4-(3-chloro-4-fluorophenylamino)-7-methoxy-6-(3-(4-morpholinyl)propoxy)quinazoline, 4-(3-ethynylphenylamino)-6,7-bis(2- methoxyethoxy)quinazoline, hormone, steroids, steroid synthetic analogs, 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, chlorotrianisene, Hydroxyprogesterone, Aminoglutethimide, Estramustine, Medroxyprogesteroneacetate, Leuprolide, Flutamide, Toremifene, Zoladex, antiangiogenics, matrix metalloproteinase inhibitors, VEGF inhibitors, ZD6474, SU6668, anti-Her2 antibodies, EGFR inhibitors, EKB-569, Imclone antibody C225, src inhibitors, bicalutamide, epidermal growth factor inhibitors, Her-2 inhibitors, MEK-1 kinase inhibitors, MAPK kinase inhibitors, P13 inhibitors, PDGF inhibitors, combretastatins, MET kinase inhibitors, MAP kinase inhibitors, inhibitors of non-receptor and receptor tyrosine kinases, inhibitors of integrin signaling, and inhibitors of insulin-like growth factor receptors.

21. The method according to claim 1, wherein the cytostatic agent is selected from the group consisting of bicalutamide, tamoxifen, 4-(3-chloro-4-fluorophenylamino)-7-methoxy-6-(3-(4-morpholinyl) propoxy)quinazoline, Her-1 inhibitors, and trastuzumab.

22. A pharmaceutical composition for the synergistic treatment of cancer which comprises one or both of a cytostatic agent and a cytotoxic agent, and also comprises a compound of formula I as described in claim 1, and a pharmaceutically acceptable carrier.

23. The composition according to claim 22 for the synergistic treatment of cancerous solid tumors.

24. The composition according to claim 22 wherein the cytotoxic agent is one or more antineoplastic agents selected from the group consisting of a microtubule-stabilizing agent, a microtubule-disruptor agent, an alkylating agent, an antimetabolite, epidophyllotoxin, an antineoplastic enzyme, a topoisomerase inhibitor, procarbazine, mitoxantrone, and a platinum coordination complex.

25. The composition according to claim 22 wherein the cytotoxic agent is one or more antineoplastic agents selected from the group consisting of an anthracycline drug, a vinca drug, a mitomycin, a bleomycin, a cytotoxic nucleoside, a taxane, an epothilone, discodermolide, a pteridine drug, a diynene, an aromatase inhibitor and a podophyllotoxin.

26. The composition according to claim 22 wherein the cytotoxic agent is one or more antineoplastic agents selected from the group consisting of paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0] heptadecane-5,9-dione, [1S-[1R*,3R*(E),7R*,10S*,11R*, 12R*,16S*]]-3-[2-[2-(aminomethyl)-4-thiazolyl]-1-methylethenyl]-7,11-dihydroxy-8,8,10,12,16-pentamethyl-4,17-dioxabicyclo-[14.1.0]heptadecane-5,9-dione, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, vindesine, leurosine, estramustine, cisplatin, carboplatin, cyclophosphamide, bleomycin, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, a pyridobenzoindole, an interferon and an interleukin.

27. The composition according to claim 22 wherein the cytotoxic agent is one or more cytotoxic agents selected from the group consisting of a taxane and an epothilone.

28. The composition according to claim 22 wherein the cytotoxic agent is one or more antineoplastic agents selected from the group consisting of paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0] heptadecane-5,9-dione and [1S-[1R*,3R*(E),7R*,10S*, 11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

29. The composition according to claim 22, wherein the cytostatic agent is selected from the group consisting of surgical castration, chemical castration, tamoxifen, 4-(3-chloro-4-fluorophenylamino)-7-methoxy-6-(3-(4-morpholinyl)propoxy)quinazoline, 4-(3-ethynylphenylamino)-6,7-bis(2-methoxyethoxy) quinazoline, hormones, steroids, steroid synthetic analogs, 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, chlorotrianisene, Hydroxyprogesterone, Aminoglutethimide, Estramustine, Medroxyprogesteroneacetate, Leuprolide, Flutamide, Toremifene, Zoladex, antiangiogenics, matrix metalloproteinase inhibitors, VEGF inhibitors, ZD6474, SU6668, anti-Her2 antibodies, EGFR inhibitors, EKB-569, Imclone antibody C225, src inhibitors, bicalutamide, epidermal growth factor inhibitors, Her-2 inhibitors, MEK-1 kinase inhibitors, MAPK kinase inhibitors, P13 inhibitors, PDGF inhibitors, combretastatins, MET kinase inhibitors, MAP kinase inhibitors, inhibitors of non-receptor and receptor tyrosine kinases, inhibitors of integrin signaling, and inhibitors of insulin-like growth factor receptors.

30. The composition according to claim 22, wherein the cytostatic agent is selected from the group consisting of bicalutamide, tamoxifen, 4-(3-chloro-4-fluorophenylamino)-7-methoxy-6-(3-(4-morpholinyl) propoxy)quinazoline, Her-1 inhibitors, and trastuzumab.

31. The composition according to claim 22 wherein
  $R_1$ is Br, or CN;
  $R_2$ is optionally substituted benzyl;
  $R_3$ is optionally substituted lower alkyl, optionally substituted phenyl, optionally substituted 2-thienyl, or optionally substituted 1-piperidinyl;
  $R_4$ is hydrogen, or methyl;
  $Z_1$ is CO, $SO_2$, or $SO_2N(R_5)$—;
  $R_5$ is optionally substituted lower alkyl, or optionally substituted phenyl; and
  n is 1.

32. The composition according to claim 22 wherein
  $R_1$ is CN;
  $R_2$ is optionally substituted benzyl;

$R_3$ is optionally substituted lower alkyl, optionally substituted phenyl, optionally substituted 2-thienyl, or optionally substituted 1-piperidinyl;

$R_4$ is hydrogen, or methyl;

Z is CO, or $SO_2$; and n is 1.

33. The composition according to claim 22 wherein $R_1$ is CN;

$R_2$ is benzyl;

$R_3$ is n-propyl, n-butyl, 3-methoxypropyl, 2-thienyl, 5-bromo-2-thienyl, phenyl, 4-methoxyphenyl, or 1-piperidinyl;

$R_4$ is hydrogen;

Z is $SO_2$; and n is 1.

34. The composition according to claim 22 wherein the formula I compound is selected from the group consisting of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile;

(R)-7-cyano-2,3,4,5-tetrahydro-1-(1H-imidazol-4-ylmethyl)4-(1-oxobutyl)-3-(phenylmethyl)-1H-1,4-benzodiazepine;

(R)-4-[(5-bromo-2-thienyl)sulfonyl]-7-cyano-2,3,4,5-tetrahydro-1-(1H-imidazol-4-ylmethyl)-3-(phenylmethyl)-1H-1,4-benzodiazepine;

(R)-7-cyano-2,3,4,5-tetrahydro-1-(1H-imidazol-4-ylmethyl)-4-[(4-methoxyphenyl)sulfonyl]-3-(phenylmethyl)-1H-1,4-benzodiazepine;

(R)-7-cyano-2,3,4,5-tetrahydro-1-(1H-imidazol-4-ylmethyl)-3-(phenylmethyl)-4-(phenylsulfonyl)-1H-1,4-benzodiazepine;

(R)-7-cyano-2,3,4,5-tetrahydro-1-(1H-imidazol-4-ylmethyl)-3-(phenylmethyl)-4-(propylsulfonyl)-1H-1,4-benzodiazepine;

(R)-4-(butylsulfonyl)-7-cyano-2,3,4,5-tetrahydro-1-(1H-imidazol-4-ylmethyl)-3-(phenylmethyl)-1H-1,4-benzodiazepine;

(R)-7-cyano-2,3,4,5-tetrahydro-1-(1H-imidazol-4-ylmethyl)-3-(phenyl methyl)-4-(1-piperidinylsulfonyl)-1H-1,4-benzodiazepine;

(R)-4-(3-methoxypropylsulfonyl)-7-cyano-2,3,4,5-tetrahydro-1-(1H-imidazol-4-yl methyl)-3-(phenyl methyl)-1H-1,4-benzodiazepine; and pharmaceutically acceptable salts thereof.

35. The composition according to claim 34 wherein the pharmaceutically acceptable salt is selected from the group consisting of the hydrochloride salt, the methanesulfonic acid salt and the trifluoroacetic acid salt.

36. The composition according to claim 34 wherein the formula I compound is (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

37. The composition according to claim 22 wherein the cytotoxic agent is paclitaxel and the formula I compound is (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

38. The composition according to claim 22 wherein the cytotoxic agent is [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione and the formula I compound is (R)-2,3,4,5-tetrahydro-1-(1H-imidazol-4-yl methyl)-3-(phenylmethyl)-4-(2-thienylsulfonyl)-1H-1,4-benzodiazepine-7-carbonitrile or a pharmaceutically acceptable salt thereof.

39. The method according to claim 1 wherein the cancer is a cancer of the prostate, the breast, a non-small cell lung cancer, a metastatic bladder cancer, a colorectal cancer, or a pancreatic cancer.

40. The composition according to claim 22 wherein the cytotoxic agent is one or more cytotoxic agents chosen from the group consisting of paclitaxel, cis-platin, carboplatin, gemcytabine, CPT-11, leucovorin, tegafur, uracil, 5-fluorouracil, 4-(3-ethynylphenylamino)-6,7-bis(2-methoxyethoxy)quinazoline, and 4-(3-chloro-4-fluorophenylamino)-7-methoxy-6-(3-(4-morpholinyl) propoxy)quinazoline).

41. The method according to claim 1 wherein said at least one cytotoxic agent is paclitaxel which is administered prior to the administration of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

42. The method according to claim 1 wherein said at least one cytotoxic agent is [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione which is administered prior to the administration of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

43. The method according to claim 1 wherein said at least one cytotoxic agent is CPT-11 which is administered prior to the administration of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

44. The method according to claim 1 wherein said at least one cytotoxic agent is gemcitabine or a pharmaceutically acceptable salt thereof which is administered prior to the administration of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

45. The method according to claim 1 wherein said at least one cytostatic agent is 4-(3-bromophenylamino)-6,7-bis(methoxy)quinazoline which is administered prior to the administration of (R)-2,3,4,5-tetrahydro-1-(1H-imidazol-4-ylmethyl)-3-(phenyl methyl)-4-(2-thienylsulfonyl)-1H-1,4-benzodiazepine-7-carbonitrile or a pharmaceutically acceptable salt thereof.

46. The method according to claim 1 wherein said at least one cytostatic agent is trastuzumab which is administered prior to the administration of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

47. The method according to claim 1 wherein said at least one cytostatic agent is 4-(3-chloro-4-fluorophenylamino)-7-methoxy-6-(3-(4-morpholinyl)propoxy)quinazoline which is administered prior to the administration of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

48. The method according to claim 1 wherein said at least one cytostatic agent is tamoxifen which is administered prior to the administration of (R)-2,3,4,5-tetrahydro-1-(1H- imidazol-4-ylmethyl)-3-(phenylmethyl)-4-(2-thienylsulfonyl)-1H-1,4-benzodiazepine-7-carbonitrile or a pharmaceutically acceptable salt thereof.

49. The method according to claim 1 wherein said at least one cytostatic agent is castration which is administered prior to the administration of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

50. The method according to claim 1 wherein said at least one cytotoxic agent is N-[5-[[[5-(1,1-dimethylethyl)-2-oxazolyl]methyl]thio]-2-thiazolyl]-4-piperidinecarboxamide or a pharmaceutically acceptable salt thereof which is administered prior to the administration of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof.

51. The method according to claim 1 wherein said at least one cytotoxic agent is paclitaxel and is administered during about a three hour infusion at about 135 mg/m2 followed by a one hour infusion of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof at about 50 mg/m2, both paclitaxel and (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof being administered at about three week intervals as needed.

52. The method according to claim 1 wherein said at least one cytotoxic agent is paclitaxel and is administered during about a one hour infusion at about 80 mg/m2 followed by about a one hour infusion of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof at about 80 mg/m2, both paclitaxel and (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof being administered at about weekly intervals as needed.

53. The method as claimed in claim 1 wherein two cytotoxic agents are administered, said cytotoxic agents being paclitaxel which is infused for about 3 hours at about 135 mg/m2 followed by about a twenty minute infusion of carboplatin at AUC equal to about 6, paclitaxel and carboplatin being administered at about three week intervals, said method further comprising about weekly administration of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile or a pharmaceutically acceptable salt thereof at about 80 mg/m2.

* * * * *